US010500166B2

United States Patent
Zerbe et al.

(10) Patent No.: US 10,500,166 B2
(45) Date of Patent: Dec. 10, 2019

(54) METHODS FOR THE TREATMENT OF ERECTILE DYSFUNCTION USING FISPEMIFENE

(71) Applicants: Robert L. Zerbe, Ann Arbor, MI (US); Alexander Bridges, Saline, MI (US); Risto Lammintausta, Turku (FI); Rochelle Hanley, Ann Arbor, MI (US); Stuart Dombey, Ann Arbor, MI (US)

(72) Inventors: Robert L. Zerbe, Ann Arbor, MI (US); Alexander Bridges, Saline, MI (US); Risto Lammintausta, Turku (FI); Rochelle Hanley, Ann Arbor, MI (US); Stuart Dombey, Ann Arbor, MI (US)

(73) Assignee: QUATRX PHARMACEUTICALS, Ann Arbor, MI (US)

( * ) Notice: Subject to any disclaimer, the term of this patent is extended or adjusted under 35 U.S.C. 154(b) by 580 days.

(21) Appl. No.: 13/848,325

(22) Filed: Mar. 21, 2013

(65) Prior Publication Data
US 2013/0217696 A1    Aug. 22, 2013

Related U.S. Application Data

(63) Continuation of application No. 12/795,986, filed on Jun. 8, 2010, now abandoned, which is a continuation of application No. 12/138,560, filed on Jun. 13, 2008, now abandoned.

(60) Provisional application No. 60/943,706, filed on Jun. 13, 2007.

(51) Int. Cl.
*A61K 31/085* (2006.01)
*A61K 31/4985* (2006.01)
*A61K 31/519* (2006.01)

(52) U.S. Cl.
CPC ........ *A61K 31/085* (2013.01); *A61K 31/4985* (2013.01); *A61K 31/519* (2013.01)

(58) Field of Classification Search
None
See application file for complete search history.

(56) References Cited

U.S. PATENT DOCUMENTS 5,750,576 A    5/1998    DeGregorio et al.
6,512,002 B2    1/2003    Lee et al.
6,576,645 B1    6/2003    Sodervall et al.
7,368,480 B2    5/2008    Podolski et al.
2006/0293294 A1    12/2006    Blom et al.
2007/0104743 A1    5/2007    Lehtola et al.

FOREIGN PATENT DOCUMENTS

WO    WO 2006/024689    *    3/2006    ............ A61K 31/00
WO    WO 2006/042409 A1    4/2006

OTHER PUBLICATIONS

Jackson (European Urol 50:426-427, 2006).*
Albrecht-Betancourt, M. "Androgen Replacement in Men with Hypoganadism and Erectile Dysfunction," Departs of Medicine and Molecular and Cellular Biology, Baylor College and VA Medical Center, Houston, TX, 2003, 1-7.
Averse, A. "Androgens Improve Cavernous Vasodilation and Response to Slidenafil in Patients with Erectile Dysfunction," Blackwell Publishing Ltd., 2003, 632-638.
Bhasin, S. "Clinical Practice Guideline—Testoterone Therapy in Adult Men with Androgen Deficiency Syndromes: An Endocine Society Clinical Practice Guideline," *J. of Clinical Endocrinology & Metabilism*, 2006, 91, 1995-2010.
Bhasin MD, S. "Testoserone Replacement and Resistance Exercise in HIV-Infected Men With Weight Loss and Low Teststerone Levels," *J. of the American Medical Association*, 2000, 283, 763-770.
Campbell, H.E. "Clinical Monograph for Drug Formulary Review: Erectile Dysfunction Agents," *JMCP J. of Managed Care Pharmacy*, 2005, 11, 151-171.
Feldman, H.A. "Impotence and Its Medical and Psychosocial Correlates: Results of the Massachusetts Male Aging Study," *American Urological Association, Inc.*, 1993, 54-61.
Guay, A.T.; Jacobson, J.; Perez J.B.; Hodge M.B.; Velasquez, E. "Clomiphene Increases Free Testoerone Levels in Men with Both Secondary Hoypoganism and Erectile Dysfunction: Who Does and Does Not Benefit?" *Int. J. of Impotence Research*, 2003, 15, 156-165.
Johannes, C.B. "Incidence of Erectile Dysfunction in Men 40 to 69 Years Old: Longitudinal Results from the Massachusetts Male Aging Study," *American Urological Association, Inc.*, 2000, 163, 460-463.
Kalinchenko, S.Y. "Oral Testoserone Undecanoate Reverses Erectile Dysfunction Associated with Diabetes Mellitus in Patients Failing on Sildenafil Citrate Therapy Alone," The Parthenon Publishing Group, 2003, 94-99.

(Continued)

*Primary Examiner* — Craig D Ricci
(74) *Attorney, Agent, or Firm* — Brinks Gilson & Lione; Ryan L. Marshall; Bashir Ali

(57) ABSTRACT

A method of treatment of erectile dysfunction (ED) comprises the step of administering fispemifene to a subject in need thereof in an amount effective to raise the subject's testosterone level. Fispemifene may be used in combination with a PDE-5 inhibitor in individuals who have failed to respond sufficiently to conventional ED treatment. Methods are also disclosed of treating ED by administering clomifene, enclomifene, ospemifene, toremifene and mixtures thereof in combination with a PDE-5 inhibitor.

12 Claims, 12 Drawing Sheets

(56) References Cited

OTHER PUBLICATIONS

McLachlan, R.I.; O'Donnell, L.; Stanton, P.G.; Balourdos, G.; Frydenberg, M.; De Kretser, D.M.; Robertson, D.M. "Effects of Testosterone Plus Medroxyprogesterone Acetate on Semen Quality, Reproductive Hormones, and Germ Cell Populations in Normal Young Men," *J. of Clinical Endocrinology and Metabolism*, 2002, 87, 546-556.

NIH Consensus Conference. "NIH Consensus Development Panel on Impotence," *J. of the American Medical Association*, 1993, 270, 83-90.

Salonia, A. "Sildenafil in Erectile Dysfunction: A Critical Review," Department of Urology, University Vita Salute San Raffaele, Milan, Italy, 2003, 19, 241-262.

Shabsigh, R. "Randomized Study of Testoeterone Gel as Adjunctive Therapy to Sildenafil in Hypogonadal Men with Erectile Dysfunction Who Do Not Respond to Sildenafil Alone," *J. of Urology*, 2004, 172, 658-663.

Shabsigh MD, R. "Testosterone Therapy in Erectile Dysfunction and Hypogonadism," Dept. of Urology, Colombia University, NY, NY, *J. Sex Med*, 2005, 2, 785-792.

Yassin, A.A. "Testosterone and Erectile Function in Hypogonadal Men Unresponsive to Tadalafil: Results form an Open-Label Uncontrolled Study," 2005, 1-8.

Non-Final Office Action from U.S. Appl. No. 12/138,560, filed Jun. 13, 2008 dated Dec. 11, 2009.

PCT Search Report for International Patent Application No. PCT/US2008/066891 dated Jan. 19, 2009.

Aversa, A.; Isidori, A.M.; De Martino, M.U.; Caprio, M.; Fabbrini, E.; Rocchietti-March, M.; Frajeset, G.; Fabbri, A. "Androgens and Penile Erection: Evidence for a Direct Relationship Between Free Testosterone and Cavernous Vasodilation in Men With Erectile Dysfunction," *Clinical Endocrinology*, 2000, 53, 517-522.

Corona, G. Mannucci, E.; Mansani, R.; Petrone, L.; Bartonlini, M.; Giommi, R.; Mancini, M.; Forti, G.; Maggi, M. "Aging and Pathogenesis of Erectile Dysfunction," *International J. of Impotence Research*, 2004, 16, 395-402.

Rajfer, J. "Relationship Between Testosterone and Erectile Dysfunction," *Reviews in Urology*, 2000, 122-128.

Boloña, E.R. et al. "Testosterone Use in Men With Sexual Dysfunction: A Systematic Review and Meta-analysis of Randomized Placebo-Controlled Trials," *Mayo Clin Proc.*, 2007, 82, 20-28.

Boyanov, M.A. et al. "Testosterone Supplementation in Men With Type 2 Diabetes, Visceral Obesity and Partial Androgen Deficiency," *The Aging Male*, 2003, 6, 1-7.

Corona, G. et al. "Psychobiologic Correlates of the Metabolic Syndrome and Associated Sexual Dysfunction," *European Urology*, 2006, 50, 595-604.

Jain, P. et al. "Testosterone Supplementation for Erectile Dysfunction: Results of a Meta-Analysis," *J. of Urology*, 2000, 164, 371-375.

\* cited by examiner

* p < 0.05,  p < 0.01, * p < 0.001 (% change vs placebo)

METHODS FOR THE TREATMENT OF ERECTILE DYSFUNCTION USING FISPEMIFENE

CROSS REFERENCE TO RELATED APPLICATIONS

This application is a Continuation of U.S. patent application Ser. No. 12/795,986, filed Jun. 8, 2010, which is a continuation of U.S. patent application Ser. No. 12/138,560, filed Jun. 13, 2008, which application claims the benefit of U.S. Provisional Application No. 60/943,706, filed Jun. 13, 2007. The disclosures of the priority applications are incorporated by reference herein in their entirety.

FIELD OF THE INVENTION

The invention relates to a method for treatment of erectile dysfunction ("ED") using fispemifene, including: the use of fispemifene as a primary treatment for ED in individuals with low testosterone; the use of fispemifene in combination with another ED drug (such as type V phosphodiesterase ("PDE-5") inhibitors) as combination therapy; and the use of fispemifene for the treatment of ED in individuals who have failed treatment with a PDE-5 inhibitor. The invention also relates to the use of selective estrogen receptor modulators (SERMs) including, but not limited to, fispemifene, clomifene, enclomifene, ospemifene, toremifene, afimoxifene, arzoxifene, bazedoxifene, lasofoxifene, ormeloxifene, raloxifene, tamoxifen, droloxifene, levormeloxifene, and idoxifene and mixtures thereof in combination with a PDE-5 inhibitor to treat ED.

BACKGROUND OF THE INVENTION

Erectile dysfunction, defined as the persistent inability to maintain an erection sufficient for satisfactory sexual performance, affects millions of men worldwide. The conventional treatment for ED is administration of a PDE-5 inhibitor, such as sildenafil, vardenafil or tadalafil. However, a significant percentage of subjects receiving PDE-5 inhibitors do not respond adequately. Approximately 30% to 50% of men receiving sildenafil, for example, do not adequately respond to therapy, such that other therapeutic options for the treatment of ED are desirable.

The reasons that some subjects do not respond to treatment with PDE-5 inhibitors are not completely known. Clearly, testosterone plays a role in ED, and may impact a subject's response to conventional ED treatment. Studies conducted in which testosterone is co-administered to ED subjects in combination with a PDE-5 inhibitor suggest that raising the testosterone level in certain individuals may improve their response to conventional ED treatment. However, testosterone treatment is associated with undesirable side effects, including prostate stimulation, gynecomastia, and adverse effects on lipid metabolism.

Thus, it further would be desirable to provide a medicine that can be co-administered with a PDE-5 inhibitor, having the effect of raising testosterone levels and improving response to ED treatment, with fewer of the deleterious side effects of exogenous testosterone treatment.

Men with chronic obstructive pulmonary disorder (COPD), HIV-infected men, and men with metabolic syndrome experience muscle wasting and low testosterone. In one study, low testosterone was observed in subjects with diabetes mellitus who failed conventional ED treatment, and some improvement was noted when the subjects were treated with testosterone together with VIAGRA® (sildenafil citrate). Muscle wasting in HIV-infected men having low testosterone was ameliorated with a combined regimen of testosterone and exercise. Thus, it further would be desirable to develop ED treatments for these individuals, which at the same time would address the concomitant problems of muscle wasting and ED.

As disclosed in U.S. Published Patent Application No. 2006/0293294, which is incorporated herein by reference, selective estrogen receptor modulators (SERMs) have been suggested as a treatment for androgen deficiency in males.

It is believed that fispemifene, which is a SERM that acts as an estrogen antagonist, as a result of its unique properties and mechanism of action, holds special attractiveness as a treatment for ED, alone or in combination with other therapies. Fispemifene, which is the generic name for (Z)-2-{2-[4-(4-Chloro-1,2-diphenylbut-1-enyl)phenoxy]ethoxy}ethanol, is a selective estrogen receptor modulator having both estrogen-like and antiestrogenic properties. Fispemifene has been shown clinically to increase serum testosterone levels in males, as described in the aforesaid U.S. Published Patent Application No. 2006/0293294, and is the most preferred agent for use in combination with a PDE-5 inhibitor, as disclosed herein.

It is believed that fispemifene acts as an antiestrogen at the level of the hypothalamic-pituitary axis, diminishing the negative feedback of estrogen, which results in the enhanced production of luteinizing hormone (LH) resulting in a subsequent increase in testosterone levels.

Based on the foregoing, fispemifene is herein proposed as a treatment for ED, alone or as adjuvant therapy with other medications. Fispemifene may be especially useful in the treatment of erectile dysfunction in men having low testosterone, as a result of age or disease condition.

Ospemifene (2-(4-((Z-4-chloro-1,2-diphenylbut-1-enyl)phenoxy) ethanol)) is a SERM which may be administered in combination with conventional ED treatment according to the present invention. Suitable forms and dosage amounts of ospemifene are disclosed in U.S. Pat. No. 5,750,576, which is incorporated herein by reference.

Clomifene (N-[2-[4-(2-chloro-1,2-diphenyl-ethenyl)phenoxy]ethyl]-N-ethyl-ethanamine) (mixture of cis- and trans-isomers) and enclomifene (trans-clomifene, or a mixture in which trans-clomifene predominates), have been proposed as agents for increasing testosterone levels. U.S. Published Patent Application No. 2004/0097597, which is incorporated by reference, proposes a dosage of trans-clomifene of about 1 to about 200 mg to increase serum testosterone, and the connection between low testosterone level and erectile dysfunction is noted, although treatment of ED per se, alone or in combination with a PDE-5 inhibitor, is not disclosed in that application.

Based on the foregoing, clomifene or enclomifene are also proposed as a combination therapy with a PDE-5 inhibitor for treatment of ED.

SUMMARY OF THE INVENTION

In one aspect, the invention is a method of treating erectile dysfunction by administering an effective amount of fispemifene to a subject in need thereof. Fispemifene is administered to raise the testosterone level of these subjects to improve erectile functioning.

In another aspect, the invention involves administering fispemifene, toremifene, clomifene, enclomifene, ospemifene or a mixture thereof, in an amount effective to increase serum testosterone to an individual undergoing ED treatment who is determined to have low testosterone. In certain embodiments, the invention relates to administering one or more selective estrogen receptor modulators (SERMs) including, but not limited to, fispemifene, clomifene, enclomifene, ospemifene, toremifene, afimoxifene, arzoxifene, bazedoxifene, lasofoxifene, ormeloxifene, raloxifene, tamoxifen, droloxifene, levormeloxifene, and idoxifene and mixtures thereof, in an amount effective to increase serum testosterone to an individual undergoing ED treatment who is determined to have low testosterone.

The individual may have low testosterone as a result of advanced age or as a result of a disease condition, for example.

In another aspect, the invention is a method a treatment of ED comprising administering fispemifene, toremifene, clomifene, enclomifene, ospemifene or a mixture thereof, to an individual in need thereof, in combination with a PDE-5 inhibitor. This may be an individual who has been determined to be insufficiently responsive to treatment with a PDE-5 inhibitor alone. In certain embodiments, the invention also relates to methods for treating ED comprising administering one or more selective estrogen receptor modulators (SERMs) including, but not limited to, fispemifene, clomifene, enclomifene, ospemifene, toremifene, afimoxifene, arzoxifene, bazedoxifene, lasofoxifene, ormeloxifene, raloxifene, tamoxifen, droloxifene, levormeloxifene, and idoxifene and mixtures thereof to an individual in need thereof, in combination with a PDE-5 inhibitor.

In still another aspect, the invention is a method of treating erectile dysfunction in an individual having low testosterone and who is suffering from chronic obstructive pulmonary disease, HIV infection, or metabolic syndrome, by administering an effective amount of fispemifene, clomifene, enclomifene, ospemifene or toremifene to said individual. In certain embodiments, the invention relates to methods for treating ED in an individual having low testosterone and who is suffering from chronic obstructive pulmonary disease, HIV infection, or metabolic syndrome, by administering an effective amount of one or more selective estrogen receptor modulators (SERMs) including, but not limited to, fispemifene, clomifene, enclomifene, ospemifene, toremifene, afimoxifene, arzoxifene, bazedoxifene, lasofoxifene, ormeloxifene, raloxifene, tamoxifen, droloxifene, levormeloxifene, and idoxifene and mixtures thereof, to said individual.

DETAILED DESCRIPTION OF THE INVENTION

Figure 1:
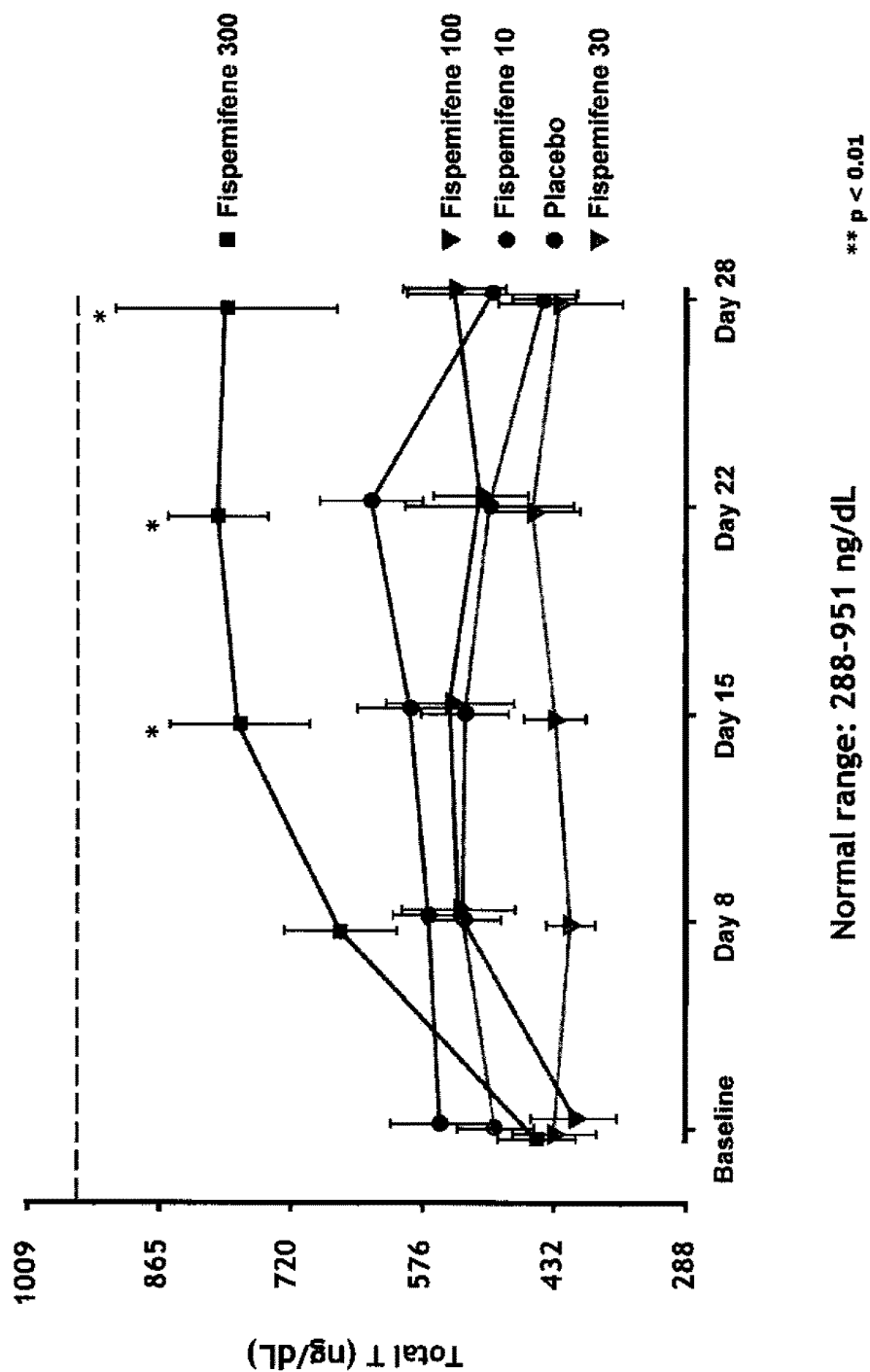
FIG. 1 depicts a graph of the data of the study from Example 1 showing the serum total testosterone (ng/dL) over time for each of the treatment groups (placebo or fispemifene 10 mg, 30 mg, 100 mg, or 300 mg/day). The bottom line on the graph is the 30 mg/day dose denoted in triangular symbols, the top line on the graph is the 300 mg/day dose denoted in square symbols, the curve second from the top is the 10 mg/day dose denoted in circular symbols. The symbol legend for each dose on the right hand margin of the graph is across from the corresponding dose value on Day 28 on the graph.
Figure 2:
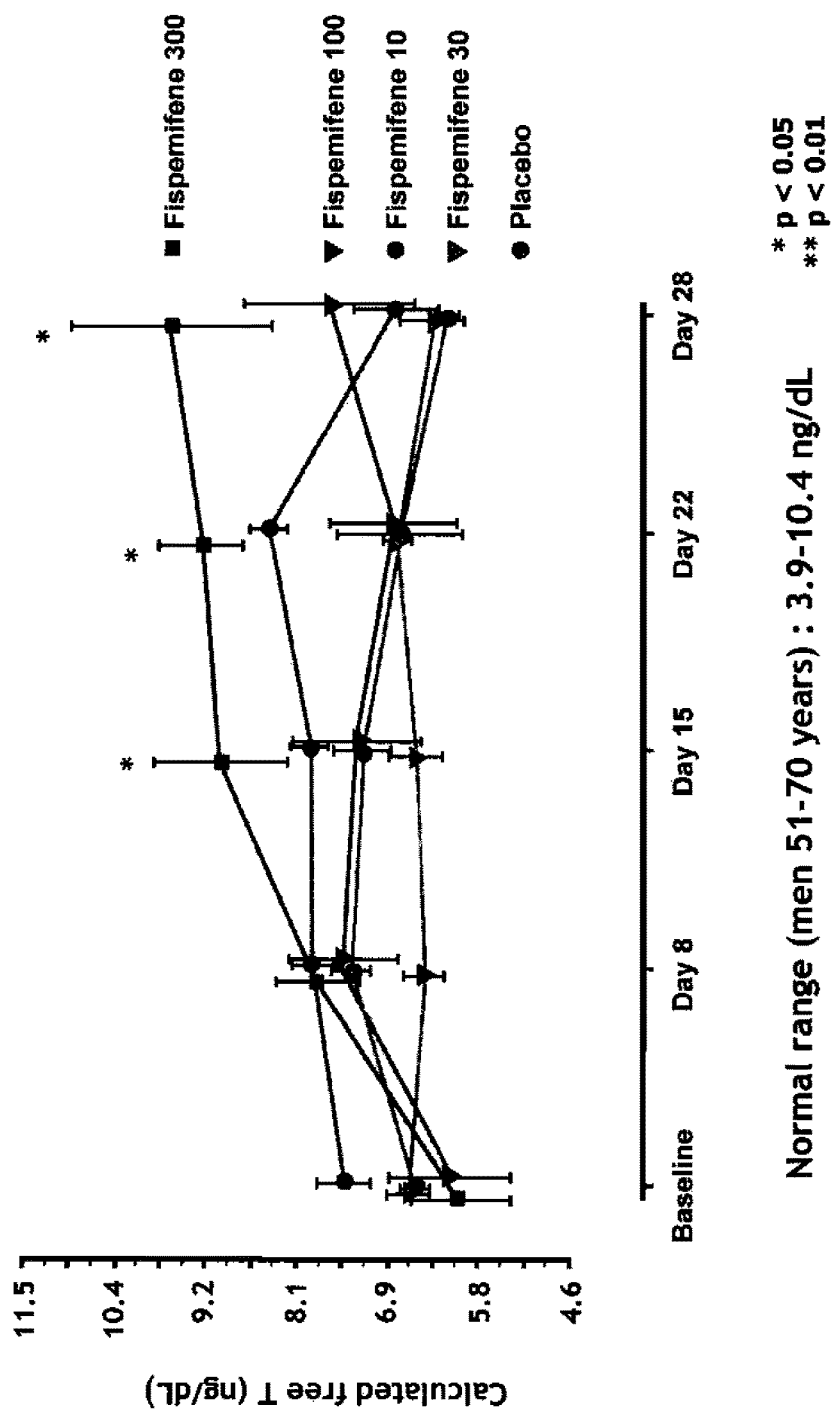
FIG. 2 depicts a graph of the data of the study from Example 1 showing the calculated serum free testosterone (ng/dL) over time for each of the treatment groups (placebo or fispemifene 10 mg, 30 mg, 100 mg, or 300 mg/day). The top line on the graph is the 300 mg/day dose denoted in square symbols, the curve second from the top is the 10 mg/day dose denoted in circular symbols. The symbol legend for each dose on the right hand margin of the graph is across from the corresponding dose value on Day 28 on the graph.
Figure 3:
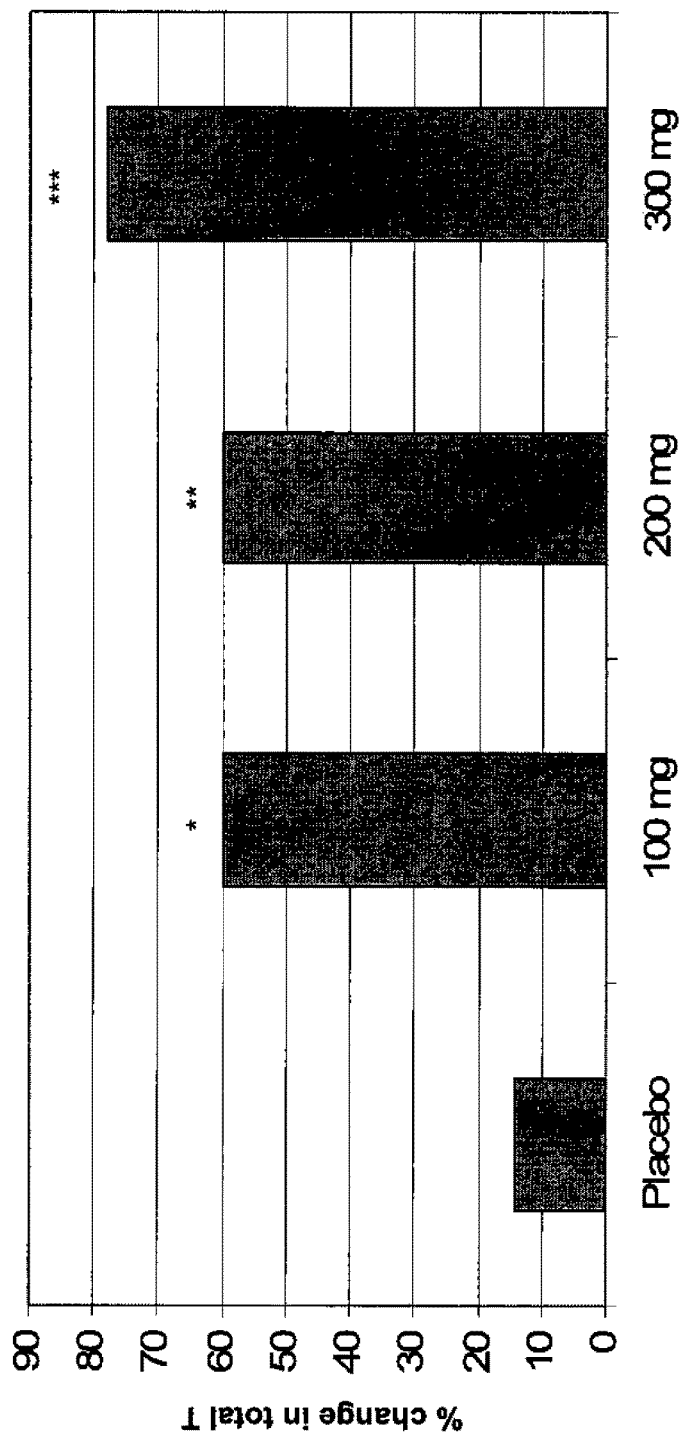
FIG. 3 depicts a graph of the data of the study from Example 3 showing the calculated mean percent change in serum total testosterone at 4 weeks for each of the treatment groups.
Figure 4:
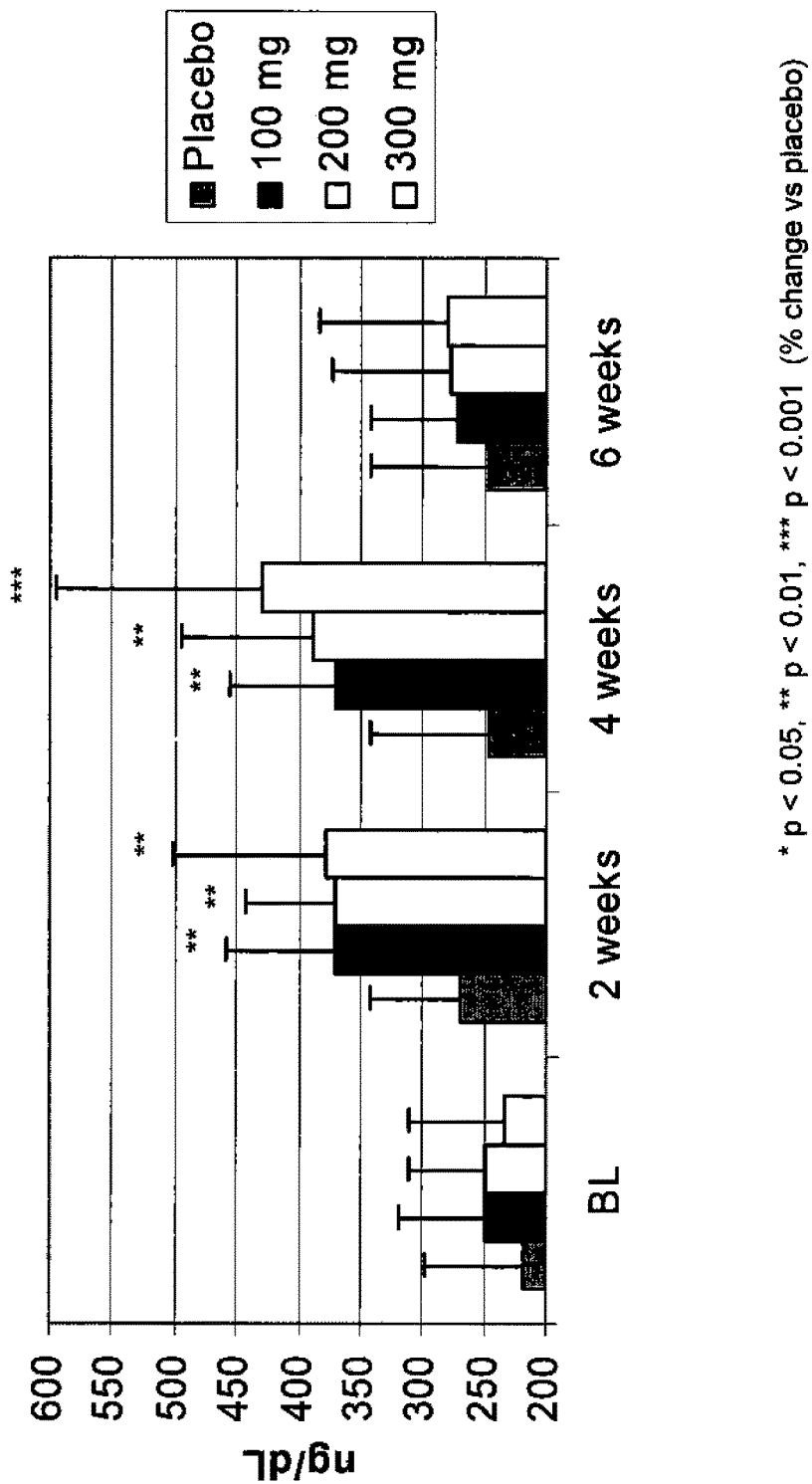
FIG. 4 depicts a graph of the data of the study from Example 3 showing the serum total testosterone versus time for each of the treatment groups. The bars from left to right for each of the BL (baseline), 2 week, 4 week, and 6 week timepoints (the 6 week timepoint occurred 2 weeks after the discontinuation of study drug at week 4) correspond to the placebo, 100 mg, 200 mg, and 300 mg/day doses, respectively.
Figure 5:
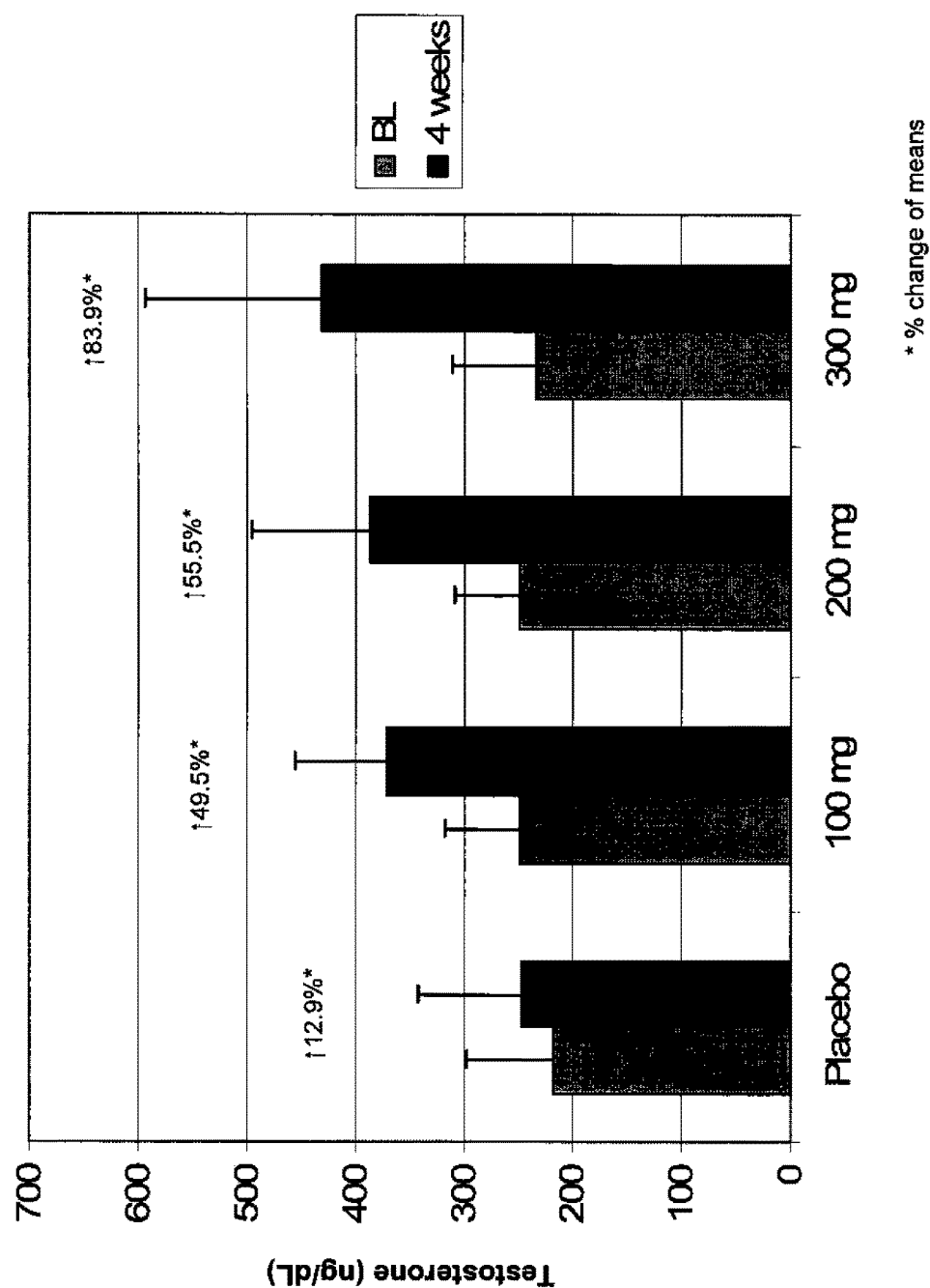
FIG. 5 depicts a graph of the data of the study from Example 3 showing serum total testosterone (ng/dL) versus dose at BL and after 4 weeks of dosing for each of the treatment groups. The bars from left to right for each of placebo, 100 mg, 200 mg, and 300 mg/day doses are the BL (baseline) and 4 week time points, respectively.
Figure 6:
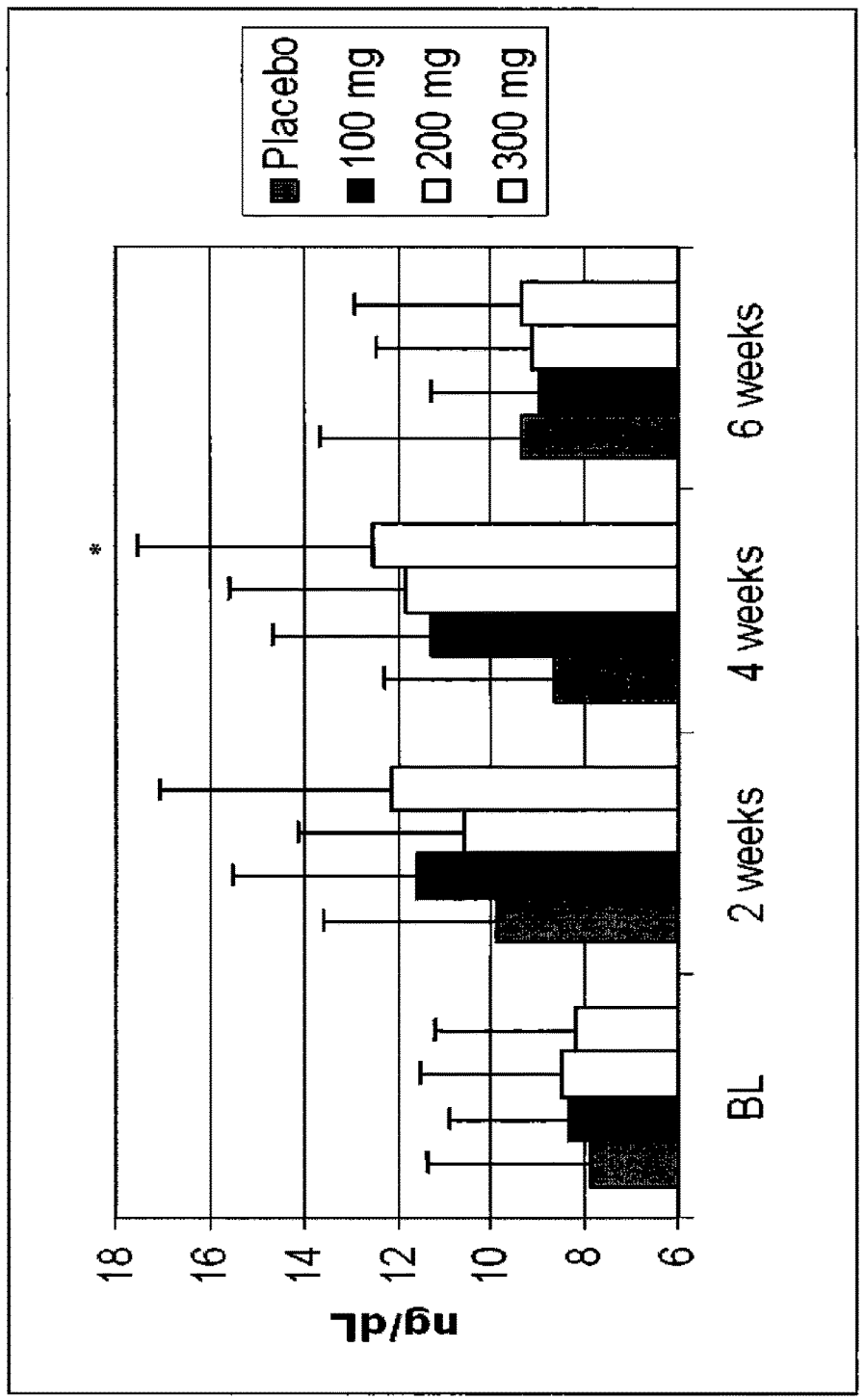
FIG. 6 depicts a graph of the data of the study from Example 3 showing serum free testosterone levels (ng/dL) measured by equilibrium dialysis over time for each of the treatment groups. The bars from left to right for each of the BL (baseline), 2 week, 4 week, and 6 week timepoints (the 6 week timepoint occurred 2 weeks after the discontinuation of study drug at week 4) correspond to the placebo, 100 mg, 200 mg, and 300 mg/day doses, respectively.
Figure 7:
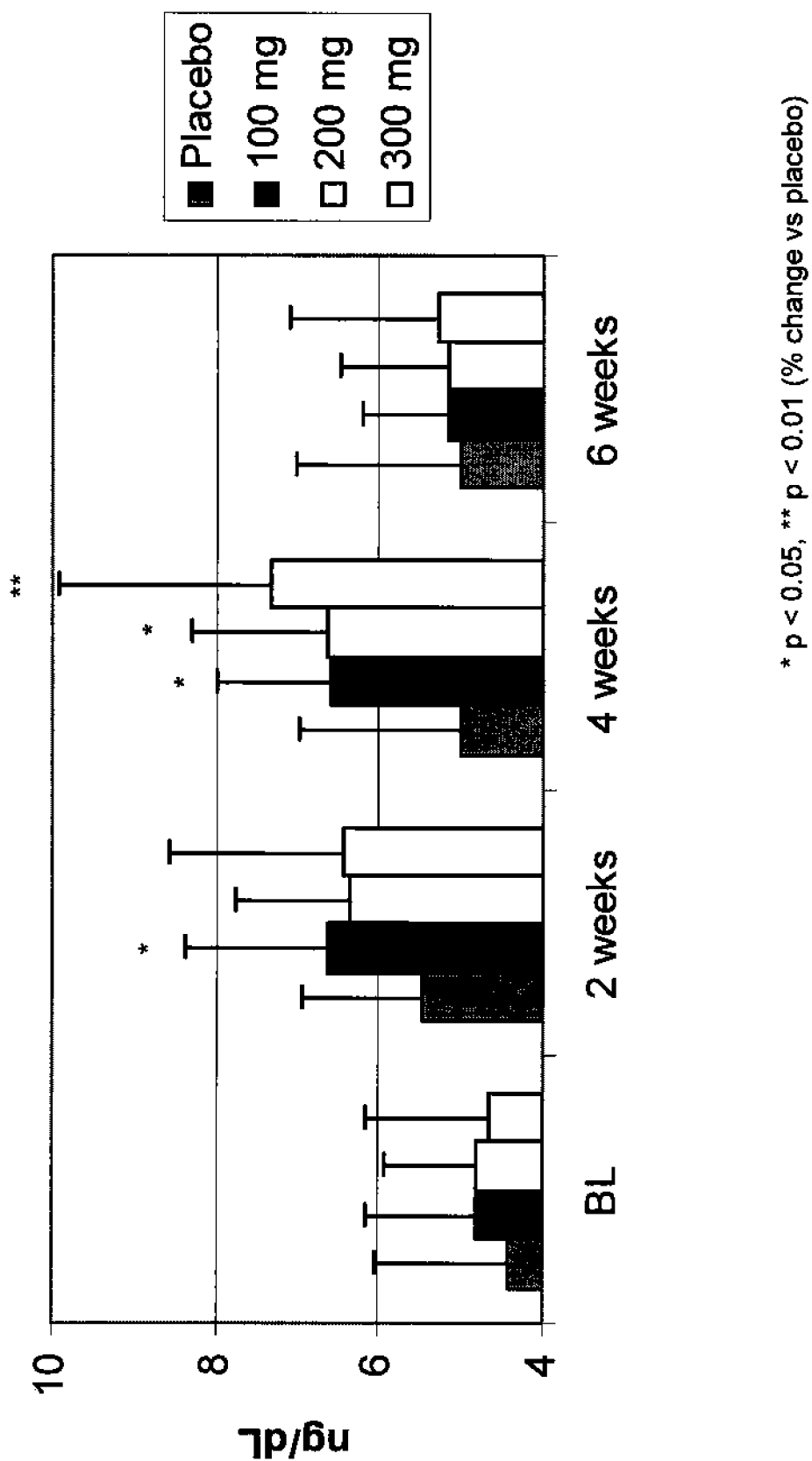
FIG. 7 depicts a graph of the data of the study from Example 3 showing the calculated serum free testosterone level (ng/dL) over time for each of the treatment groups. The bars from left to right for each of the BL (baseline), 2 week, 4 week, and 6 week timepoints (the 6 week timepoint occurred 2 weeks after the discontinuation of study drug at week 4) correspond to the placebo, 100 mg, 200 mg, and 300 mg/day doses, respectively.
Figure 8:
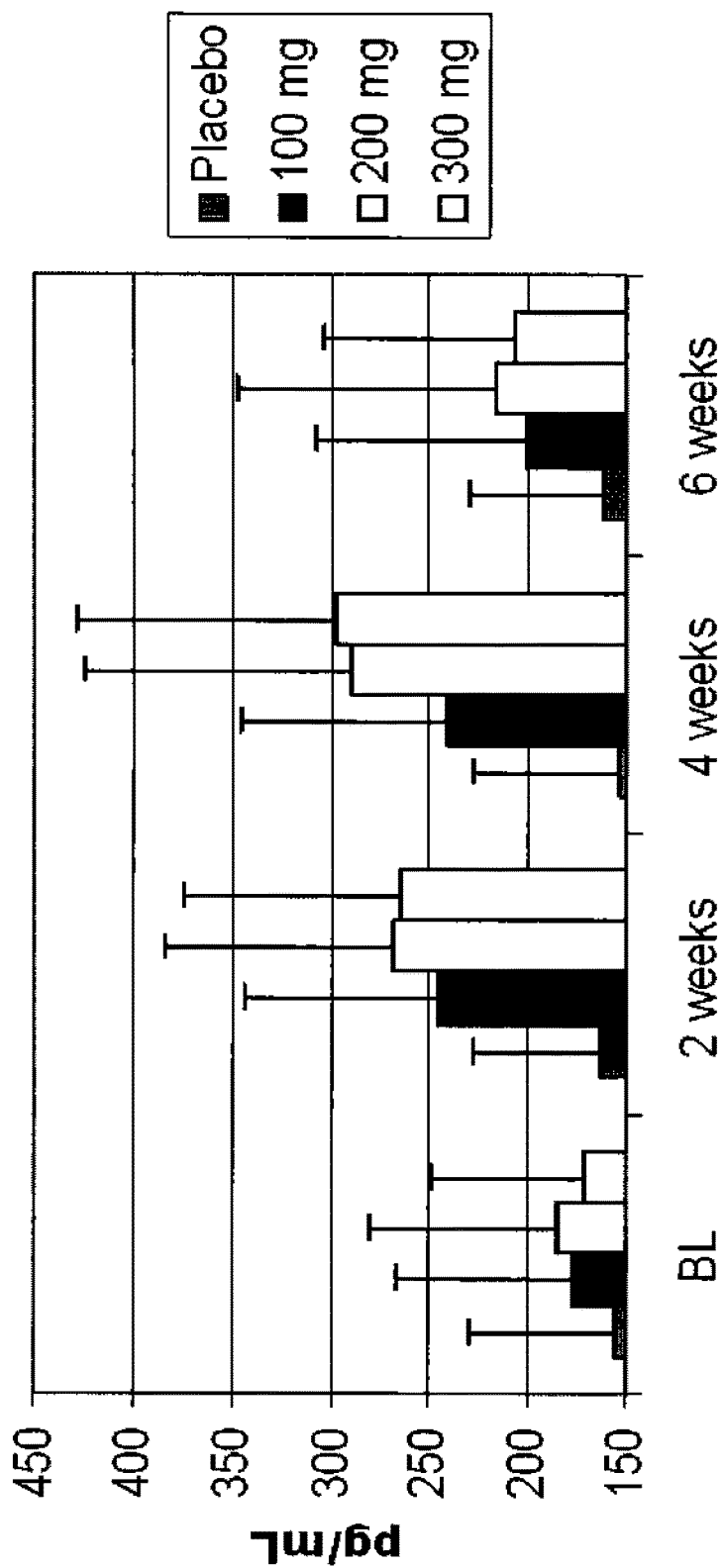
FIG. 8 depicts a graph of the data of the study from Example 3 showing the serum DHT (dihydrotestosterone) (pg/mL) levels over time for each of the treatment groups. The bars from left to right for each of the BL (baseline), 2 week, 4 week, and 6 week timepoints (the 6 week timepoint occurred 2 weeks after the discontinuation of study drug at week 4) correspond to the placebo, 100 mg, 200 mg, and 300 mg/day doses, respectively.
Figure 9:
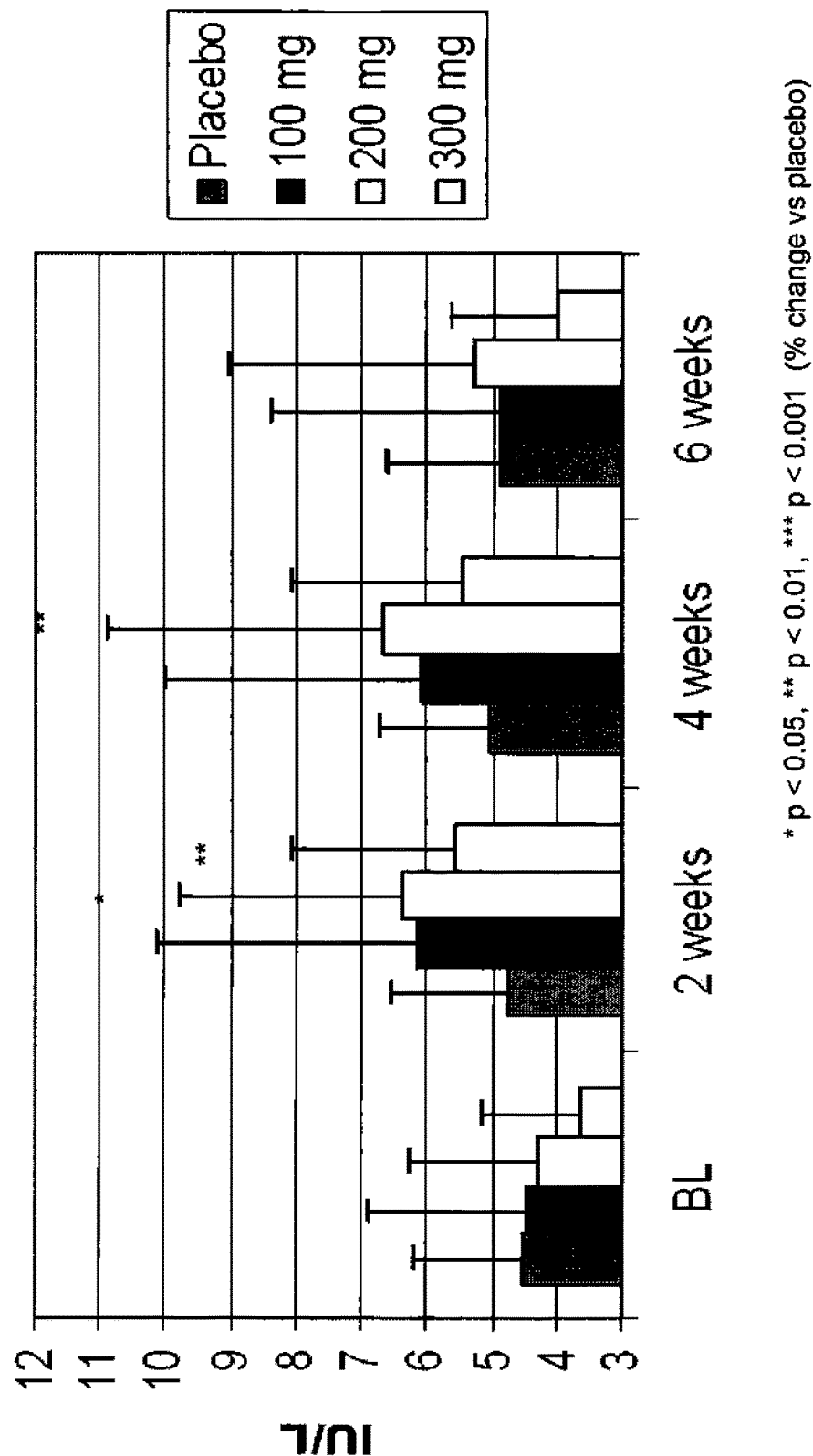
FIG. 9 depicts a graph of the data of the study from Example 3 showing the serum LH (luteinizing hormone) level (IU/L) over time for each of the treatment groups. The bars from left to right for each of the BL (baseline), 2 week, 4 week, and 6 week timepoints (the 6 week timepoint occurred 2 weeks after the discontinuation of study drug at week 4) correspond to the placebo, 100 mg, 200 mg, and 300 mg/day doses, respectively.
Figure 10:
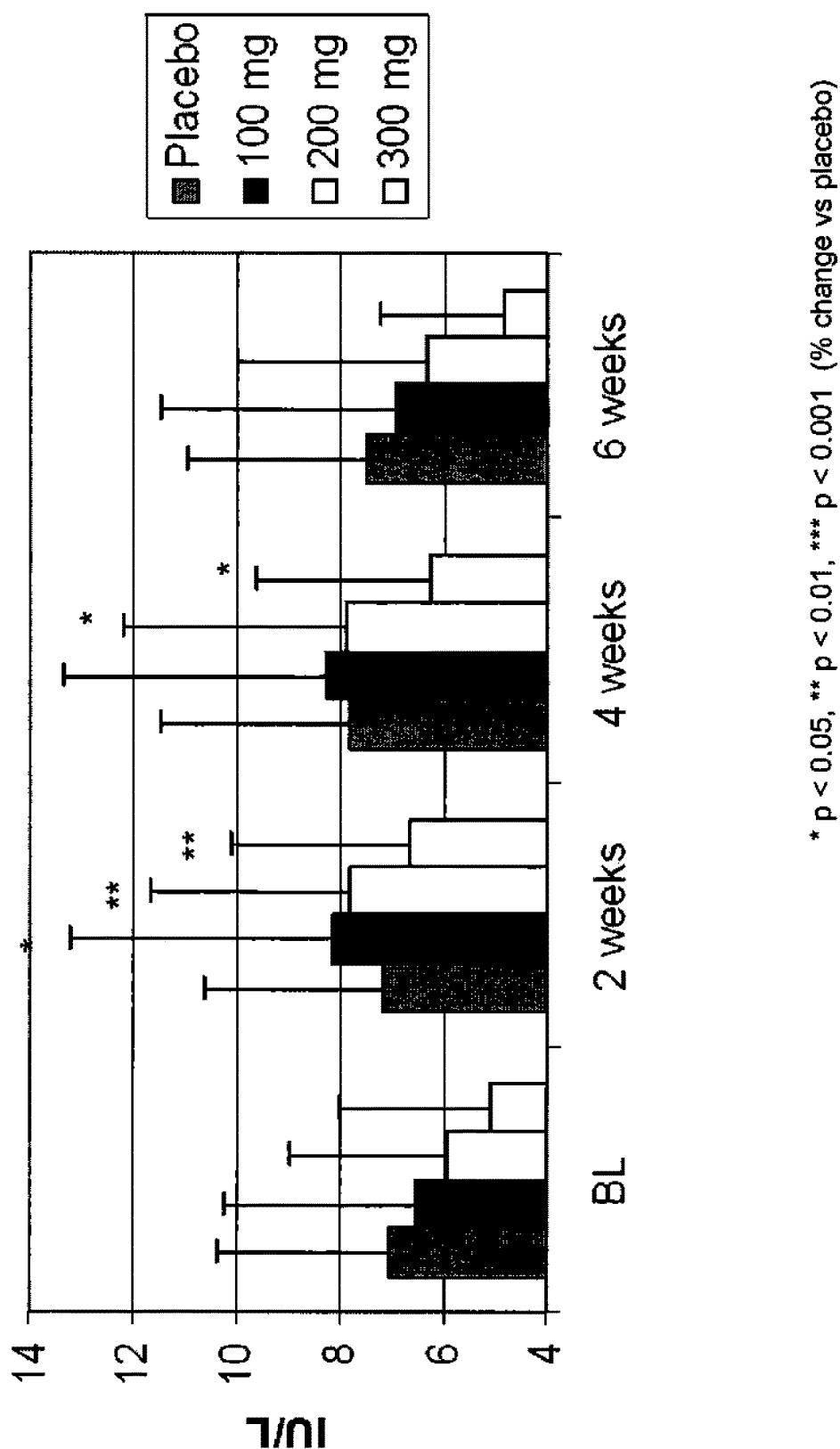
FIG. 10 depicts a graph of the data of the study from Example 3 showing the serum FSH (follicle stimulating hormone) level (IU/L) over time for each of the treatment groups. The bars from left to right for each of the BL (baseline), 2 week, 4 week, and 6 week timepoints (the 6 week timepoint occurred 2 weeks after the discontinuation of study drug at week 4) correspond to the placebo, 100 mg, 200 mg, and 300 mg/day doses, respectively.
Figure 11:
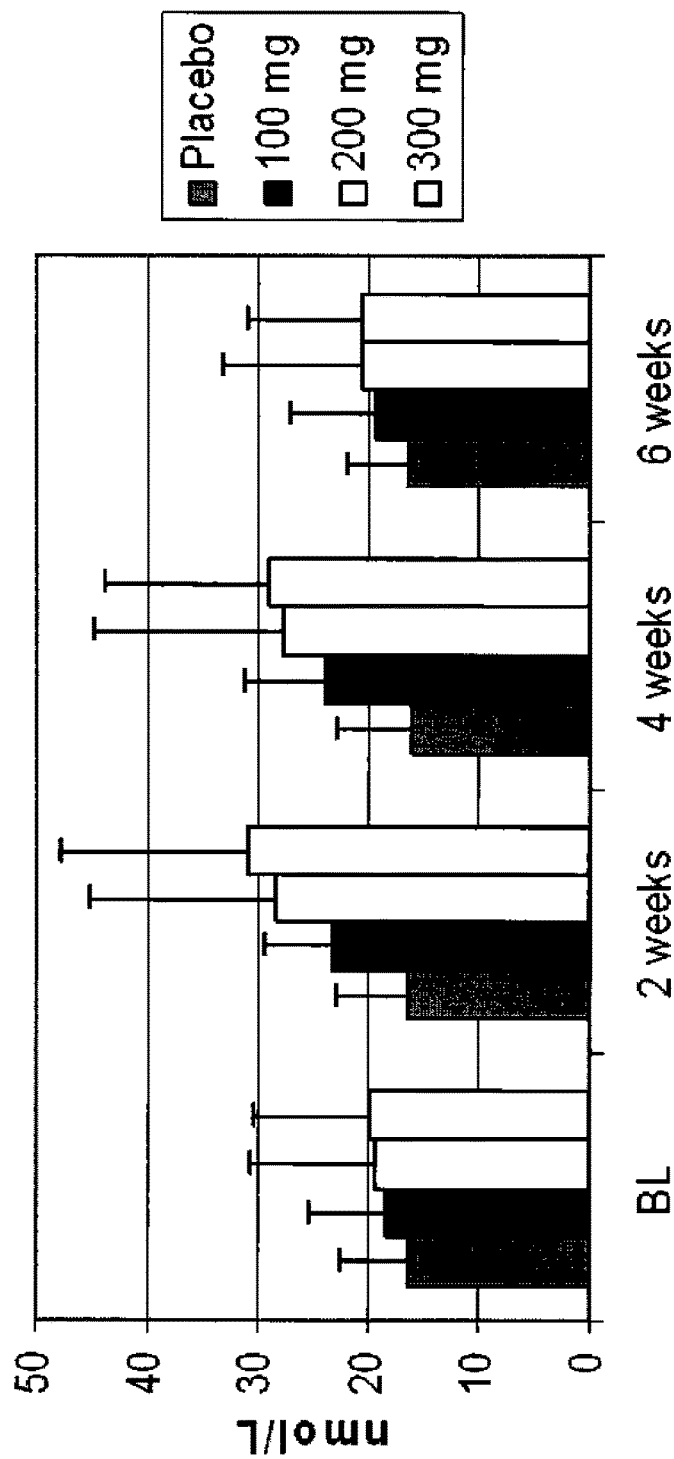
FIG. 11 depicts a graph of the data of the study from Example 3 showing the serum sex hormone-binding globulin level (nmol/L) over time for each of the treatment groups. The bars from left to right for each of the BL (baseline), 2 week, 4 week, and 6 week timepoints (the 6 week timepoint occurred 2 weeks after the discontinuation of study drug at week 4) correspond to placebo, 100 mg, 200 mg, and 300 mg doses, respectively.
Figure 12:
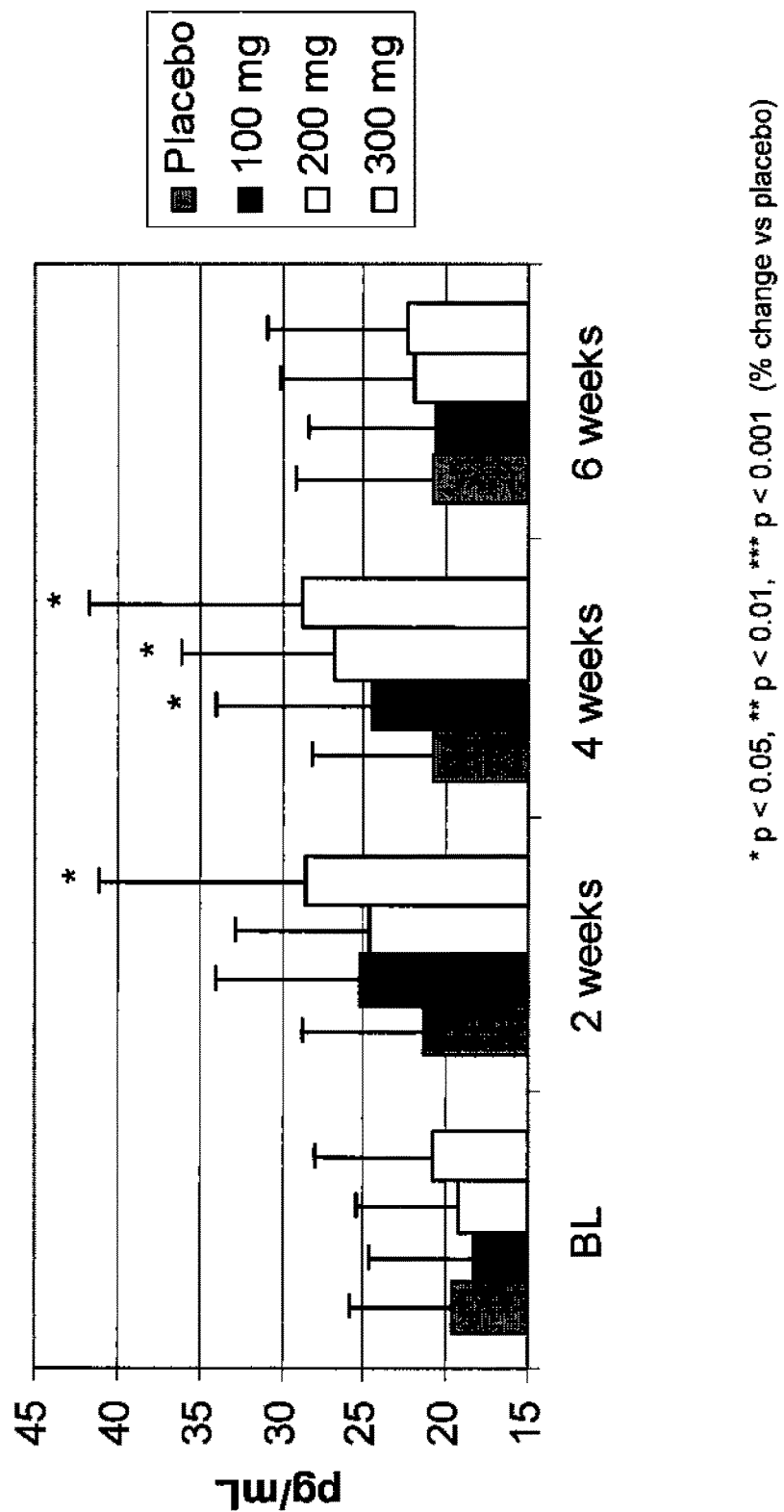
FIG. 12 depicts a graph of the data of the study from Example 3 showing the serum estradiol levels (pg/mL) over time for each of the treatment groups. The bars from left to right for each of the BL (baseline), 2 week, 4 week, and 6 week timepoints (the 6 week timepoint occurred 2 weeks after the discontinuation of study drug at week 4) correspond to the placebo, 100 mg, 200 mg, and 300 mg/day doses, respectively.

The androgens, of which testosterone is the principal agent, are male sex hormones, responsible for the development of the masculine sex characteristics. Defects in cavernosal tissue arising from testosterone deficiency can impair erectile capacity.

A shortage of testosterone (hypogonadism) may be classified into two principal forms, which are designated primary and secondary hypogonadism. Primary hypogonadism is the lack of testosterone production or a decreased testosterone production within the body originating from a malfunction of the testes, which are the main synthetic location for testosterone. Primary hypogonadism includes testicular failure due to congenital or acquired anorchia, XYY Syndrome, XX males, Noonan Syndrome, gonadal dysgenesis, Leydig cell tumors, maldescended testes, varicocele, Sertoli-Cell-Only Syndrome, cryptorchidism, bilateral torsion, vanishing testis syndrome, orchiectomy, Klinefelter Syndrome, chemotherapy, toxic damage from alcohol or heavy metals, and general disease (renal failure, liver cirrhosis, diabetes, myotonia dystrophica). Patients with primary hypogonadism show an intact feedback mechanism in that the low serum testosterone concentrations are associated with high FSH (follicle-stimulating hormone) and LH (luteinizing hormone) concentrations. However, because of testicular or other failures, the high LH concentrations are not effective at stimulating testosterone production.

Secondary (or hypogonadotrophic) hypogonadism arises where the main reason for the low testosterone level is a malfunction of the hypothalamus or the hypophysis. This involves an idiopathic gonadotropin or LH-releasing hormone deficiency. This type of hypogonadism includes Kallman Syndrome, Prader-Labhart-Willi Syndrome, Laurence-Moon-Biedl Syndrome, pituitary insufficiency/adenomas, Pasqualini Syndrome, hemochromatosis, hyperprolactinemia, or pituitary-hypothalamic injury from tumors, trauma, radiation, or obesity. Because patients with secondary hypogonadism do not demonstrate an intact feedback pathway, the lower testosterone concentrations are not associated with increased LH or FSH levels. Thus, these men have low testosterone serum levels but have gonadotropins in the normal to low range.

Men experience a slow but continuous decline in average serum testosterone after approximately age 20 to 30 years (age-related testosterone deficiency). Researchers estimate that the decline is about 1-2% per year. Moreover, as men age, the circadian rhythm of testosterone concentration is often muted, dampened, or completely lost.

The normal ranges for testosterone concentration vary as well as the definition of the limit value to diagnose hypogonadism. For the purposes herein, unless otherwise stated: if serum total testosterone levels are >400 ng/dL (i.e., 14 nmol/L), there is no testosterone deficiency and this is referred to as a "normal testosterone level;" if total serum testosterone level is <400 ng/dL, the subject may be considered to have a "low testosterone level." An "effective amount" of an agent in connection with raising testosterone, is the minimum amount required to achieve an increase in testosterone level, whether or not testosterone is raised to a normal level. In some instances, it may be preferable to define low testosterone as <250 ng/dL or <300 ng/dL.

Erectile function is commonly evaluated by tabulating responses provided to the International Index of Erectile Function ("IIEF"). The IIEF is a validated self-administered questionnaire used to assess therapeutic efficacy of an ED treatment. The IIEF is composed of five domains: erectile function, libido, orgasmic function, sexual satisfaction and overall satisfaction. Other questionnaires may be utilized, including the Sexual Health Inventory for Men (SHIM), which is an abbreviated form of the IIEF; and the Sexual Encounter Profile (SEP), which involves questions of both the subject and the subject's partner. As used herein, a directional improvement in any component of these criteria is considered "treatment," and the minimum dosage required to obtain such improvement is defined herein as an "effective amount." For example, an important criterion of success of an ED therapy may be determined to be the frequency of successful intercourse; and an increase in that frequency, whether or not statistically significant, may be deemed a successful treatment. Alternatively, improvement may be measured by changes over various domains of the IIEF, such as an increase in libido, or in overall satisfaction. These improvements also constitute examples of "treatment," and the minimum dosage required to achieve improvement on one or more of these axes is an "effective amount." The administration of fispemifene, enclomifene, ospemifene, clomifene or toremifene to treat ED has particular relevance when administered in combination with a PDE-5 inhibitor to a subject who continues to have symptoms of ED despite treatment with a PDE-5 inhibitor. In certain embodiments, the administration of selective estrogen receptor modulators (SERMs) including, but not limited to, fispemifene, clomifene, enclomifene, ospemifene, toremifene, afimoxifene, arzoxifene, bazedoxifene, lasofoxifene, ormeloxifene, raloxifene, tamoxifen, droloxifene, levormeloxifene, and idoxifene and mixtures thereof to treat ED has particular relevance when administered in combination with a PDE-5 inhibitor to a subject who continues to have symptoms of ED despite treatment with a PDE-5 inhibitor.

Clinically, a subject is meaningfully suboptimally responsive to treatment with a PDE-5 inhibitor when the subject scores 21 or less (corresponding to a disease severity of mild-to-moderate or worse) on the IIEF Erectile Function domain despite PDE-5 inhibitor treatment. In general, a subject is suboptimally responsive to PDE-5 inhibitor treatment when the subject attempts and fails to complete sexual intercourse over the course of several weeks, notwithstanding treatment with a PDE-5 inhibitor. The administration of fispemifene, enclomifene, ospemifene, clomifene or toremifene to treat ED has particular relevance when administered in combination with a PDE-5 inhibitor to a subject who is unresponsive to treatment with a PDE-5 inhibitor. Clinically, a subject is unresponsive to treatment with a PDE-5 inhibitor when the subject receives a score of 2 or 3 on questions 3 and 4 of the IIEF during a screening visit. In general, a subject is not responsive to PDE-5 inhibitor treatment when the subject attempts and fails to complete sexual intercourse over the course of several weeks, notwithstanding treatment with a PDE-5 inhibitor.

Thus, a method of treating ED according to the invention may comprise (1) a step of administering a PDE-5 inhibitor to a subject in need thereof and observing a failure of the subject to respond; and (2) a step of administering fispemifene, clomifene, enclomifene, ospemifene, toremifene, or a mixture thereof, in combination with a PDE-5 inhibitor. A method of the invention may also comprise (1) a step of administering a PDE-5 inhibitor to a subject in need thereof and observing a failure of the subject to respond; and (2) a step of administering one or more selective estrogen receptor modulators (SERMs) including, but not limited to, fispemifene, clomifene, enclomifene, ospemifene, toremifene, afimoxifene, arzoxifene, bazedoxifene, lasofoxifene, ormeloxifene, raloxifene, tamoxifen, droloxifene, levormeloxifene, and idoxifene and mixtures thereof in combination with a PDE-5 inhibitor.

The above method of treating ED according to the invention may further comprise a step of measuring the testosterone level of the subject, as follows: (1) a step of administering a PDE-5 inhibitor to a subject in need thereof and observing a failure of a subject to have an adequate response; (2) measuring the serum testosterone level of the subject to determine that the level is less than 400 ng/dL, or otherwise determining that the subject has low androgen levels (such as by measuring free testosterone); and (3) a step of administering fispemifene, clomifene, enclomifene, ospemifene, toremifene, or a mixture thereof, in combination with a PDE-5 inhibitor. These steps may also be performed in a different order, such as: first diagnosing the subject with erectile dysfunction and hypogonadism; and then treating with fispemifene, clomifene, enclomifene, ospemifene, toremifene, or a mixture thereof and observing that the subject has a suboptimal response; and finally a step of administering fispemifene, clomifene, enclomifene, ospemifene, toremifene, or a mixture thereof, in combination with a PDE-5 inhibitor.

Fispemifene, enclomifene, ospemifene, clomifene and toremifene may improve muscle wasting experienced by HIV-infected men experiencing weight loss and low testosterone. Accordingly, these SERMs may be used in conjunction with other agents in ED treatment of HIV-infected men.

Fispemifene, enclomifene, ospemifene, clomifene and toremifene may be administered in combination with other ED agents to raise the testosterone levels of subjects with metabolic syndrome (and the like) and improve their symptoms of ED. In addition, one or more selective estrogen receptor modulators (SERMs) including, but not limited to, fispemifene, clomifene, enclomifene, ospemifene, toremifene, afimoxifene, arzoxifene, bazedoxifene, lasofoxifene, ormeloxifene, raloxifene, tamoxifen, droloxifene, levormeloxifene, and idoxifene and mixtures thereof, may be administered in combination with other ED agents to raise the testosterone levels of subjects with metabolic syndrome (and the like) and improve their symptoms of ED.

PDE-5 inhibitor as used herein includes any agent which inhibits the type 5 cGMP-specific PDE5 enzyme, including without limitation, sildenafil, vardenafil and tadalafil, which are commercially recognized treatment agents for ED, all of which are typically taken orally. Other PDE-5 inhibitors include those disclosed in U.S. Pat. No. 6,512,002 B2, incorporated by reference.

Fispemifene has been demonstrated to raise testosterone levels and may be administered alone to treat ED in men. A suitable dosage is expected to be in a range of about 5 mg/day to about 1500 mg/day. In a phase I repeated dose study, twenty-three healthy men aged 50 to 70 years received daily 10 mg, 30 mg 100 mg and 300 mg dosages of fispemifene for 28 days. Fispemifene was well tolerated at all dose levels. The adverse events reported more than once included upper respiratory tract infection, nausea and abdominal pain. All other adverse events were single cases. Fispemifene at the 100 and 300 mg/day dose levels increased serum total testosterone levels 32% and 75% respectively. Thus, a preferred dosage range of fispemifene to treat ED is expected to be 10 to 1000 mg/day.

As described above, fispemifene, clomifene, enclomifene, ospemifene or toremifene (all of which are SERMs), or a mixture thereof, may be administered in combination with a PDE-5 inhibitor to men who are unresponsive to treatment with PDE-5 inhibitors alone. In addition, selective estrogen receptor modulators (SERMs) including, but not limited to, fispemifene, clomifene, enclomifene, ospemifene, toremifene, afimoxifene, arzoxifene, bazedoxifene, lasofoxifene, ormeloxifene, raloxifene, tamoxifen, droloxifene, levormeloxifene, and idoxifene and mixtures thereof, may be administered in combination with a PDE-5 inhibitor to men who are unresponsive to treatment with PDE-5 inhibitors alone.

In this context "administered in combination" means: (1) part of the same unitary dosage form; (2) administration separately, but as part of the same therapeutic treatment program or regimen, typically but not necessarily, on the same day. In a preferred embodiment, the SERM and PDE-5 inhibitor are administered in combination as a fixed daily dosage. The combination of fispemifene (or other SERM) with a PDE-5 inhibitor as a unitary dosage form is a novel composition according to the invention.

Alternatively, fispemifene, clomifene or toremifene may be administered at a fixed daily dosage, and the PDE-5 inhibitors taken on an as needed basis, in advance of expected sexual activity, usually not more than once daily.

When fispemifene is administered as adjuvant therapy with a PDE-5 inhibitor, a preferred daily dosage is about 10 mg to 1000 mg, more preferably 10 mg to 300 mg.

When enclomifene is administered as a combination therapy with a PDE-5 inhibitor, a suitable daily dosage is about 1 to 200 mg. Clomifene is expected to be suitable at a daily dose of up to 100 mg in combination with a PDE-5 inhibitor.

A suitable daily oral dosage of PDE-5 inhibitor is believed to be in range of 25 to 100 mg for sildenafil; 5 to 20 mg for vardenafil; and 2.5 to 20 mg for tadalafil. However, the invention is not limited to these dosage ranges, and the suitable dosage amount for these well known and extensively studied compounds is considered to be within the skill in the art.

The invention is not limited to particular administration forms of the active agents described herein. For example, oral formulations, parenteral injections, transdermal, buccal and rectal formulations may be used. Oral formulations include, without limitation, powders, tablets, caplets, and gelatin capsules. Oral formulations of both the PDE-5 inhibitor (which are commercially available) and the SERM are preferred. Suitable oral formulations of fispemifene are described in U.S. Published Application No. 2007/0104743, which is incorporated by reference.

Reference to the active agents described herein includes reference to their pharmaceutically acceptable salts. For example, sildenafil is commercially available as sildenafil citrate. Reference to any PDE-5 inhibitor herein refers also to salts of the active agent, as disclosed in U.S. Pat. No. 6,512,002 (incorporated by reference). Likewise, reference to SERMs includes reference to their salts, as disclosed in U.S. Pat. Nos. 5,750,576 and 6,576,645, which are incorporated by reference.

The invention will be illustrated by the following non-restrictive Experimental Section.

EXPERIMENTAL

Example 1

Fispemifene has been studied in two phase I studies in humans—in a single dose and a repeated dose study. Effect of fispemifene on hormone levels was one main focus of the repeated dose study. The phase I repeated dose study (number 101-50202) was a randomized, double-blind, placebo-controlled 28-day dose-escalation study performed in 31 healthy, elderly men, aged 50-68 years. The main objective of the study was to investigate the tolerability, safety and pharmacokinetics of fispemifene after repeated oral doses, but the study focused also on the effects of fispemifene on serum free and total testosterone, estradiol, and other relevant hormones. The fispemifene doses 10, 30, 100 and 300 mg per day and placebo were administered once every morning as capsules containing 10 mg or 100 mg of fispemifene, or placebo. The dose was escalated to the next higher dose level, if the previous dose had been safe and well tolerated evaluated by the laboratory safety determinations and ultrasound of mammary glands.

The variables for safety and tolerability were adverse events, vital signs, 12-lead ECG, clinical laboratory evaluations, physical examination, ultrasound examinations (mammary glands) and inhibin B. For pharmacokinetics, the concentrations of fispemifene and its metabolite(s) were to be evaluated. For pharmacodynamics, serum concentrations of FSH, LH, estradiol, testosterone, SHBG, prolactin, aldosterone, cortisol and TSH before and during treatment were measured and compared with the concentrations in the placebo-group.

Results on the Effects of Fispemifene on Hormones

Fispemifene increased the serum concentrations of testosterone, FSH, LH, and SHBG (Table 1) during the 28 days of treatment. Testosterone was increased statistically significantly with 100 mg and 300 mg fispemifene compared with placebo. With the 300 mg dose, the increase in the mean total testosterone was about 75% compared to the baseline concentration. Two out of six men treated with the highest fispemifene dose had their serum testosterone level above the upper limit of normal range (i.e., 33 nmol/L) during treatment. The other four had a significant increase within the reference range. All the six men had normal testosterone value at baseline. With the 100 mg dose, the increase of the mean total testosterone was about 32%, and all the six men in the group had their testosterone level increased within the reference range. The increase in total testosterone levels in serum is illustrated by group in FIG. 1. There were no safety concerns raised with any dose suggesting that even a higher dose could be utilized if deemed appropriate.

Serum total testosterone concentrations (mean and SD) and the other hormones at baseline and during treatment in the fispemifene study 101-50202 by dose.

TABLE 1

Serum total testosterone concentrations (mean and SD) and the other hormones at baseline and during treatment in the fispemifene study 101-50202 by dose.

|  | Placebo | | Fispemifene 10 mg | | Fispemifene 30 mg | | Fispemifene 100 mg | | Fispenifene 300 mg | |
| --- | --- | --- | --- | --- | --- | --- | --- | --- | --- | --- |
|  | Mean | SD | Mean | SD | Mean | SD | Mean | SD | Mean | SD |
| Testosterone (nmol/L) | | | | | | | | | | |
| Baseline | 17.25 | 4.2 | 19.33 | 4.7 | 15.00 | 3.5 | 14.27 | 4.0 | 15.67 | 3.6 |
| Day 8 | 18.50 | 4.1 | 19.83 | 3.31 | 4.40 | 2.1 | 18.67 | 5.3 | 23.17 | 5.2 |
| Day 15 | 18.43 | 4.4 | 20.50 | 4.9 | 15.00 | 2.7 | 19.00 | 6.0 | 27.00 | 6.5 |
| Day 22 | 17.50 | 8.5 | 22.00 | 4.4 | 15.80 | 3.9 | 17.83 | 4.5 | 27.83 | 4.7 |
| Day 28 | 15.43 | 3.2 | 17.40 | 7.2 | 14.80 | 5.3 | 18.83 | 4.8 | 27.50 | 10.3 |
| FSH (U/L) | | | | | | | | | | |
| Baseline | 5.60 | 3.4 | 5.42 | 3.6 | 9.14 | 13.4 | 6.30 | 5.6 | 6.80 | 5.4 |
| Day 8 | 5.65 | 2.9 | 5.87 | 4.2 | 9.78 | 14.2 | 7.68 | 7.8 | 8.80 | 7.6 |
| Day 15 | 4.67 | 1.6 | 5.20 | 2.9 | 10.14 | 14.6 | 8.10 | 9.0 | 8.73 | 7.2 |
| Day 22 | 4.47 | 1.6 | 6.60 | 4.1 | 10.18 | 15.1 | 8.20 | 9.0 | 8.85 | 8.1 |
| Day 28 | 4.29 | 1.7 | 5.66 | 3.7 | 8.42 | 11.6 | 7.73 | 7.9 | 7.57 | 7.0 |
| LH (U/L) | | | | | | | | | | |
| Baseline | 3.11 | 1.6 | 3.47 | 1.0 | 3.58 | 2.0 | 4.12 | 1.9 | 4.58 | 2.7 |
| Day 8 | 3.29 | 0.8 | 3.12 | 1.5 | 4.26 | 2.2 | 5.52 | 4.2 | 6.80 | 3.5 |
| Day 15 | 3.31 | 0.9 | 2.87 | 1.1 | 5.02 | 2.4 | 6.82 | 7.5 | 6.75 | 4.6 |
| Day 22 | 2.80 | 0.8 | 3.56 | 1.2 | 4.32 | 2.3 | 7.18 | 8.3 | 7.77 | 6.6 |
| Day 28 | 2.71 | 0.9 | 3.02 | 0.9 | 4.42 | 2.0 | 7.60 | 9.6 | 6.70 | 4.8 |
| Estradiol (pmol/L) | | | | | | | | | | |
| Baseline | 100.6 | 31.2 | 106.2 | 20.9 | 97.8 | 17.9 | 84.3 | 22.6 | 102.5 | 30.0 |
| Day 8 | 93.8 | 17.1 | 94.7 | 31.2 | 105.6 | 29.8 | 108.3 | 28.9 | 104.0 | 20.0 |
| Day 15 | 85.0 | 31.6 | 81.7 | 25.4 | 102.4 | 22.2 | 111.5 | 48.2 | 97.8 | 26.9 |
| Day 22 | 75.0 | 32.4 | 116.6 | 15.1 | 99.6 | 20.4 | 106.3 | 37.4 | 95.5 | 32.9 |
| Day 28 | 73.6 | 32.6 | 75.0 | 20.1 | 87.0 | 22.2 | 94.5 | 48.4 | 89.7 | 30.9 |
| SHBG (nmol/L) | | | | | | | | | | |
| Baseline | 49.1 | 18.6 | 47.7 | 19.9 | 34.2 | 12.8 | 41.7 | 29.4 | 50.7 | 15.1 |
| Day 8 | 44.5 | 16.1 | 46.3 | 21.1 | 34.2 | 12.2 | 47.7 | 35.2 | 64.2 | 21.3 |

TABLE 1-continued

Serum total testosterone concentrations (mean and SD) and the other hormones at baseline and during treatment in the fispemifene study 101-50202 by dose.

|  | Placebo | | Fispemifene 10 mg | | Fispemifene 30 mg | | Fispemifene 100 mg | | Fispenifeme 300 mg | |
|---|---|---|---|---|---|---|---|---|---|---|
|  | Mean | SD | Mean | SD | Mean | SD | Mean | SD | Mean | SD |
| Day 15 | 46.0 | 19.1 | 48.2 | 22.8 | 37.4 | 20.8 | 52.0 | 39.5 | 66.2 | 21.1 |
| Day 22 | 44.9 | 18.4 | 50.2 | 27.1 | 37.2 | 19.2 | 55.7 | 45.3 | 65.2 | 14.8 |
| Day 28 | 45.0 | 18.5 | 45.2 | 24.3 | 36.6 | 19.1 | 50.8 | 42.8 | 58.3 | 12.3 |

Discussion and Conclusions

Fispemifene induced a clinically and statistically significant and dose dependent increase in the serum testosterone concentration in healthy older men within 28 days from the start of the treatment. Also, within the 28-day treatment period, the increase in testosterone serum concentration was seen in all the subjects treated with 100 mg or 300 mg fispemifene. An increase of 75% from baseline can be considered clinically highly significant, and thus clinical benefits in men with low testosterone can be expected. The increases also in LH and FSH suggest that fispemifene has an antiestrogenic effect on hypothalamus/hypophysis, and that the increase in testosterone occurs due to the increase in the hypophyseal hormones. The increase in testosterone is moderate and, therefore, no harmful effects often associated with external testosterone administration are expected. Furthermore, a SERM is likely to provide protection against the possible safety problems of testosterone like development of prostate cancer. Thus, a SERM increasing testosterone provides an optimal treatment for hypogonadism, balancing the efficacy and safety of the increased testosterone.

Example 2

This is a prophetic example. Subjects would be selected from men, all over twenty years of age, unresponsive to PDE-5 inhibitor treatment as demonstrated by responses on the IIEF for a 28 day lead-in period, having morning total testosterone level less than or equal to 400 ng/dL. Half of the subjects would be assigned to the fispemifene treatment group (fispemifene plus sildenafil) and half will be assigned to the placebo control group (sildenafil without fispemifene). Subjects would self administer fispemifene once daily in the morning after breakfast for 8 weeks. Subjects would take sildenafil 100 mg on an as needed basis when sexual activity is anticipated.

The following observations would be expected: increases in total testosterone levels from baseline to week 4 to week 8; improvement in IIEF erectile function domain score from baseline to week 4 to week 8; improvement in other IIEF domain scores from baseline to week 4 to week 8.

Example 3

A randomized, double-blind, placebo controlled, parallel-group study of once-daily doses of fispemifene (100, 200, and 300 mg/day) given for 4 weeks was conducted in a population of hypogonadal men. Subjects were required to meet all of the following inclusion criteria at screening and prior to randomization to be eligible for the study:

1. The subject had signed a written informed consent to participate in the study and had agreed to follow dosing instructions and complete all required study visits;
2. The subject was a male ≥40 years of age at the time of randomization.
3. The subject had a screening total testosterone level and a confirmatory baseline total testosterone level ≤350 ng/dL. Testosterone levels were determined from early morning (0700 h to 0900 h) specimens; and
4. The subject had a serum LH level of 1.7-15.0 IU/L and an FSH level of 1.5-15.0 IU/L at the screening visit.

Subjects were excluded from the study if they had an elevated serum prolactin level, if they had evidence of benign prostatic hypertrophy, or if they were taking medications that affected the hypothalamic-pituitary-gonadal axis and had not adequately washed off.

There were 77 subjects total. The number of subjects randomized to the 100 mg fispemifene, 200 mg fispemifene, 300 mg fispemifene, and placebo arms were 21, 21, 19, and 16, respectively.

Subjects were randomly assigned to one of four treatment groups in a 1:1:1:1 ratio:

Treatment A (100 mg): fispemifene 100 mg+placebo+placebo;
Treatment B (200 mg): fispemifene 100 mg+fispemifene 100 mg+placebo;
Treatment C (300 mg): fispemifene 100 mg+fispemifene 100 mg+fispemifene 100 mg; and
Treatment D (Placebo): placebo+placebo+placebo.

Subjects took one dose (three capsules) of study medication once a day at home for 4 weeks. Capsules were to be taken in the morning immediately after breakfast, with the exception of the morning of the Week 4 visit. Capsules were not to be taken on the morning of the Week 4 visit because trough plasma levels of fispemifene were determined by a blood sample taken at this visit. Each subject was randomly assigned to treatment with one of the 3 different dose regimens of fispemifene or placebo vehicle. Each subject received a 4 week supply of study drug.

Blood samples were taken from the subjects within 1 week prior to dosing with study drug to establish baseline values; after 2 and 4 weeks of randomization; and 2 weeks after the last dose of study drug. Serum was prepared from those samples and used to determine the mean % change from baseline in total testosterone, free testosterone, SHBG (sex hormone-binding globulin), DHT (dihydrotestosterone), E2 (estradiol), LH (luteinizing hormone), FSH (follicle stimulating hormone), and inhibin B.

The primary efficacy endpoint was defined as percent change from baseline in morning total testosterone levels at Week 4. The intent-to-treat ("ITT") population was the primary population for analysis. The secondary efficacy endpoints included:

1. Percent change from baseline in free testosterone and calculated free testosterone at Weeks 2, 4, and 6;
2. Percent change from baseline in total testosterone levels at Weeks 2 and 6; and
3. Percent change from baseline in SHBG, DHT, E2, LH, FSH, inhibin B, and testosterone/E2 ratio at Weeks 2, 4, and 6.

These values are graphed in FIGS. 3-12 and are also shown below in table format in Tables 2-15 with the standard deviation from the mean ("S.D.").

Essentially, fispemifene induced a clinically and statistically significant and dose dependent increase to, but not beyond, the normal range in the serum total testosterone concentration within 14 days from the start of the treatment; and this increase was maintained during the treatment period. Serum FSH, LH, and estradiol levels were also increased, confirming the observations in Example 1 and lending further support to the proposed mechanism by which fispemifene raises serum testosterone levels (i.e., that it has antiestrogenic effect on hypothalamus/hypophysis, leading to an increase in the hypophyseal hormones, and thus to an increase in testosterone).

It was also confirmed that the increase in testosterone is moderate and, therefore, that the drug has a lesser likelihood of safety problems or abuse than exogenously-administered testosterone.

TABLE 2

Primary Efficacy Analysis: Morning Total Testosterone Levels (ng/dL) for Intent-to-Treat Subjects

| Study Week | Statistics N | Fispemifene | | | Placebo | Overall P-value | Pairwise Comparisons | | |
| --- | --- | --- | --- | --- | --- | --- | --- | --- | --- |
| | | 100 mg 21 | 200 mg 21 | 300 mg 19 | 16 | | 100 mg vs. Placebo | 200 mg vs. Placebo | 300 mg vs. Placebo |
| Actual Value at Baseline (Visit 2) | Mean ± SD | 248.6 ± 68.90 | 249.1 ± 60.90 | 234.2 ± 77.69 | 218.6 ± 79.13 | 0.531[1] | 0.228[1] | 0.258[1] | 0.461[1] |
| | Median | 266.0 | 253.0 | 246.0 | 227.5 | | | | |
| | Min, Max | 101.0, 347.0 | 133.0, 334.0 | 17.0, 348.0 | 58.0, 334.0 | | | | |
| Actual Value at Week 4 | Mean ± SD | 371.6 ± 83.36 | 387.3 ± 107.39 | 430.7 ± 163.39 | 246.9 ± 95.26 | NA | NA | NA | NA |
| | Median | 353.0 | 372.0 | 479.0 | 265.5 | | | | |
| | Min, Max | 246.0, 535.0 | 241.0, 626.0 | 8.0, 643.0 | 40.0, 397.0 | | | | |
| % Change from Baseline to Week 4 | Mean ± SD | 0.60 ± 0.524 | 0.60 ± 0.390 | 0.78 ± 0.536 | 0.14 ± 0307 | <0.001[1] | 0.010[1] | 0.002[1] | <0.001[1] |
| | Median | 0.35 | 0.60 | 0.80 | 0.14 | | | | |
| | Min, Max | 0.07, 1.98 | −014, 127 | −0.53, 1.81 | −0.31, 0.74 | | | | |

% Change front Baseline is defined as (Week 4 minus Baseline) divided by Baseline. Missing values for ITT subjects are replaced via LOCF approach.

NA = Not Applicable (not planned).

[1]P-values for treatment comparisons from non-parametric approach (Kruskal-Wallis test for overall comparisons and Wilcoxon test for pairwise comparisons).

TABLE 3

Descriptive Summary: Free Testosterone (ng/dL) by Visit for Intent-to-Treat Subjects

| Study Week | Statistics | Fispemifene | | | Placebo (N = 16) |
| --- | --- | --- | --- | --- | --- |
| | | 100 mg (N = 21) | 200 mg (N = 21) | 300 mg (N = 19) | |
| Baseline (Visit 2) | N (%) Reported | 21 (100.0%) | 21 (100.0%) | 19 (100.0%) | 16 (100.0%) |
| | Mean ± SD | 8.35 ± 2.536 | 8.48 ± 3.043 | 8.19 ± 2.966 | 7.83 ± 3.490 |
| | Median | 8.40 | 8.50 | 8.20 | 8.35 |
| | Min, Max | 3.20, 12.20 | 4.30, 15.90 | 0.30, 12.30 | 2.00, 13.20 |
| Week 2 (Visit 4) | N (%) Reported | 19 (90.5%) | 21 (100.0%) | 19 (100.0%) | 14 (87.5%) |
| | Mean ± SD | 11.6 ± 3.93 | 10.6 ± 3.52 | 12.1 ± 4.96 | 9.86 ± 3.710 |
| | Median | 10.3 | 10.0 | 12.9 | 9.90 |
| | Min, Max | 5.7, 17.7 | 4.8, 16.4 | 0.2, 22.0 | 3.70, 18.20 |
| Week 4 (Visit 5) | N (%) Reported | 21 (100.0%) | 21 (100.0%) | 19 (100.0%) | 16 (100.0%) |
| | Mean ± SD | 11.3 ± 3.40 | 11.8 ± 3.80 | 12.5 ± 5.00 | 8.64 ± 3.668 |
| | Median | 10.8 | 12.2 | 14.0 | 8.35 |
| | Min, Max | 6.4, 18.2 | 5.2, 19.4 | 0.1, 21.2 | 1.80, 14.70 |
| Week 6 (Visit 6) | N (%) Reported | 21 (100.0%) | 21 (100.0%) | 19 (100.0%) | 16 (100.0%) |
| | Mean ± SD | 893 ± 2.300 | 9.10 ± 3.307 | 9.30 ± 3.567 | 9.36 ± 4.330 |
| | Median | 9.80 | 8.00 | 9.80 | 8.55 |
| | Min, Max | 4.90, 13.30 | 5.40, 16.80 | 0.30, 17.30 | 1.80, 18.30 |

TABLE 4

Secondary Efficacy Analysis: Free Testosterone (ng/dL) for Intent-to-Treat Subjects

| Category | Study Week | Statistics | Fispemifene 100 mg (N = 21) | Fispemifene 200 mg (N = 21) | Fispemifene 300 mg 0 = 19) | Placebo (N = 16) |
|---|---|---|---|---|---|---|
| Descriptive Summaries | Actual Value at Baseline (Visit 2) | N (%) Reported | 21 (100.0%) | 21 (100.0°%) | 19 (100.0%) | 16 (100.0%) |
| | | Mean ± SD | 8.35 ± 2.536 | 8.48 ± 3.043 | 8.19 ± 2.966 | 7.83 ± 3.490 |
| | | Median | 8.40 | 8.50 | 8.20 | 8.35 |
| | | Min, Max | 3.20, 12.20 | 4.30, 15.90 | 030, 12.30 | 2.00, 13.20 |
| | % Change from Baseline to Week 2 | N (%) Reported | 19 (90.5%) | 21 (100.0%) | 19 (100.0%) | 14 (87.5%) |
| | | Mean ± SD | 040 ± 0.387 | 0.30 ± 0.422 | 0.43 ± 0.340 | 0.26 ± 0.338 |
| | | Median | 0.30 | 019 | 0.43 | 0.12 |
| | | Min, Max | −0.13, 1.22 | −0.16, 1.83 | −0.33, 1.00 | −0.07, 1.19 |
| | % Change from Baseline to Week 4 | N (%) Reported | 21 (100.0%) | 21 (100.0%) | 19 (100.0%) | 16 (100.0%) |
| | | Mean ± SD | 0.44 ± 0.490 | 0.47 ± 0.483 | 0.48 ± 0.452 | 0.17 ± 0.385 |
| | | Median | 0.38 | 0.41 | 0.40 | 0.05 |
| | | Min, Max | −0.17, 2.08 | −0.17, 1.52 | −0.67, 1.22 | −0.31, 1.05 |
| | % Change from Baseline to Week 6 | N (%) Reported | 21 (100.0%) | 21 (100.0%) | 19 (100.0%) | 16 (100.0%) |
| | | Mean = SD | 0.18 ± 0.548 | 0.16 ± 0.479 | 0.16 ± 0.308 | 0.25 ± 0.406 |
| | | Median | −0.03 | 0.03 | 0.06 | 0.15 |
| | | Min, Max | −0.38, 2.16 | −0.60, 1.31 | −0.37, 1.02 | −0.31, 1.10 |
| P-values[1] for Comparing Treatments Over Time | | All Arms | 0.664 | — | — | — |
| | | 100 mg vs. Placebo | 0.304 | — | — | — |
| | | 200 mg vs. Placebo | 0.409 | — | — | — |
| | | 300 mg vs. Placebo | 0.245 | — | — | — |

% Change from Baseline is defined as (Week 2, 4 or 6 minus Baseline) divided by Baseline. Missing values for ITT subjects are replaced via LOCF approach.
[1]P-values for comparing treatment groups over time from a repeated-measures analysis of variance model via PROC MIXED with % change as response variable and terms of treatment, visit (study week), and treatment by visit interactions.

TABLE 5

Descriptive Summary: Calculated Free Testosterone (ng/dL) by Visit for Intent-to-Treat Subjects

| Study Week | Statistics | Fispemifene 100 mg (N = 21) | Fispemifene 200 mg (N = 21) | Fispemifene 300 mg (N = 19) | Placebo (N = 16) |
|---|---|---|---|---|---|
| Baseline (Visit 2) | N (%) Reported | 21 (100.0%) | 21 (100.0%) | 18 (94.7%) | 16 (100.0%) |
| | Mean ± SD | 4.81 ± 1.368 | 4.80 ± 1.143 | 4.66 ± 1.509 | 4.41 ± 1.646 |
| | Median | 4.95 | 4.70 | 4.94 | 4.36 |
| | Min, Max | 2.19, 7.54 | 2.66, 7.29 | 0.23, 7.02 | 1.10, 6.94 |
| Week 2 (Visit 4) | N (%) Reported | 19 (90.5%) | 21 (100.0%) | 19 (100.0%) | 14 (87.5%) |
| | Mean ± SD | 6.64 ± 1.732 | 6.37 ± 1.386 | 6.43 ± 2.152 | 5.46 ± 1.480 |
| | Median | 6.46 | 6.21 | 7.25 | 5.68 |
| | Min, Max | 4.32, 10.27 | 4.11, 8.98 | 0.14, 9.79 | 2.66, 7.90 |
| Week 4 (Visit 5) | N (%) Reported | 21 (100.0%) | 21 (100.0%) | 19 (100.0%) | 16 (100.0%) |
| | Mean ± SD | 6.59 ± 1.396 | 6.64 ± 1.658 | 7.33 ± 2.589 | 5.01 ± 1.984 |
| | Median | 6.63 | 6.39 | 8.40 | 4.99 |
| | Min, Max | 4.15, 9.13 | 4.05, 9.83 | 0.10, 10.31 | 0.83, 7.93 |
| Week 6 (Visit 6) | N (%) Reported | 21 (100.0%) | 21 (100.0%) | 19 (100.0%) | 16 (100.0%) |
| | Mean ± SD | 5.15 ± 1.057 | 5.153 ± 1.328 | 5.29 ± 1.791 | 5.01 ± 2.001 |
| | Median | 5.10 | 4.88 | 5.44 | 4.87 |
| | Min, Max | 2.57, 7.05 | 3.60, 7.81 | 0.22, 8.02 | 0.83, 8.09 |

TABLE 6

Secondary Efficacy Analysis: Calculated Free Testosterone (ng/dL) for Intent-to-Treat Subjects

| Category | Study Week | Statistics | Fispemifene 100 mg (N = 21) | Fispemifene 200 mg (N = 21) | Fispemifene 300 mg (N = 19) | Placebo (N = 16) |
|---|---|---|---|---|---|---|
| Descriptive Summaries | Actual Value at Baseline (Visit 2) | N (%) Reported | 21 (100.0%) | 21 (100.0%) | 18 (94.7%) | 16 (100.0%) |
| | | Mean ± SD | 4.81 ± 1.368 | 4.80 ± 1.143 | 4.66 ± 1.509 | 4.41 ± 1.646 |
| | | Median | 4.95 | 4.70 | 4.94 | 4.36 |
| | | Min, Max | 2.19, 7.54 | 2.66, 7.29 | 0.23, 7.02 | 1.10, 6.94 |

TABLE 6-continued

Secondary Efficacy Analysis: Calculated Free Testosterone (ng/dL) for Intent-to-Treat Subjects

|  |  |  | Fispemifene | | | |
|---|---|---|---|---|---|---|
| Category | Study Week | Statistics | 100 mg (N = 21) | 200 mg (N = 21) | 300 mg (N = 19) | Placebo (N = 16) |
|  | % Change from Baseline to Week 2 | N (%) Reported | 19 (90.5%) | 21 (100.0%) | 18 (94.7%) | 14 (87.5%) |
|  |  | Mean ± SD | 0.42 ± 0.292 | 0.36 ± 0.321 | 0.38 ± 0.262 | 0.23 ± 0.327 |
|  |  | Median | 0.36 | 0.28 | 0.40 | 0.08 |
|  |  | Min, Max | 0.08, 1.00 | 0.01, 1.24 | −0.37, 0.83 | −0.05, 0.99 |
|  | % Change from Baseline to Week 4 | N (%) Reported | 21 (100.0%) | 21 (100.0%) | 18 (94.7%) | 16 (100.0%) |
|  |  | Mean ± SD | 0.46 ± 0.449 | 0.41 ± 0.324 | 0.56 ± 0.430 | 0.15 ± 0.305 |
|  |  | Median | 0.36 | 0.40 | 0.59 | 0.14 |
|  |  | Min, Max | −0.00, 1.57 | −0.15, 1.12 | −0.58, 1.33 | −0.30, 0.78 |
|  | % Change from Baseline to Week 6 | N (%) Reported | 21 (100.0%) | 21 (100.0%) | 18 (94.7%) | 16 (100.0%) |
|  |  | Mean ± SD | 0.14 ± 0.344 | 0.11 ± 0.314 | 0.17 ± 0.276 | 0.15 ± 0.357 |
|  |  | Median | 0.08 | 0.06 | 0.10 | 0.06 |
|  |  | Min, Max | −0.26, 1.15 | −0.37, 0.75 | −0.26, 0.65 | −0.30, 1.08 |
| P-values[1] for Comparing Treatments Over Time | | All Arms | 0.217 | — | — | — |
|  |  | 100 mg vs. Placebo | 0.094 | — | — | — |
|  |  | 200 mg vs. Placebo | 0.184 | — | — | — |
|  |  | 300 mg vs. Placebo | 0.048 | — | — | — |

% Change from Baseline is defined as (Week 2, 4 or 6 minus Baseline) divided by Baseline. Missing values for ITT subjects are replaced via LOCF approach.
[1]P-values for comparing treatment groups over time from a repeated-measures analysis of variance model via PROC MIXED with % change as response variable and terms of treatment, visit (study week), and treatment by visit interactions.

TABLE 7

Descriptive Summary: Total Testosterone (ng/dL) by Visit for Intent-to-Treat Subjects

|  |  | Fispemifene | | | |
|---|---|---|---|---|---|
| Study Week | Statistics | 100 mg (N = 21) | 200 mg (N = 21) | 300 mg (N = 19) | Placebo (N = 16) |
| Baseline (Visit 2) | N (%) Reported | 21 (100.0%) | 21 (100.0%) | 19 (100.0%) | 16 (100.0%) |
|  | Mean ± SD | 248.6 ± 68.90 | 249.1 ± 60.90 | 234.2 ± 77.69 | 218.6 ± 79.13 |
|  | Median | 266.0 | 253.0 | 246.0 | 227.5 |
|  | Min, Max | 101.0, 347.0 | 133.0, 334.0 | 17.0, 348.0 | 58.0, 334.0 |
| Week 2 (Visit 4) | N (%) Reported | 19 (90.5%) | 21 (100.0%) | 19 (100.0%) | 14 (87.5%) |
|  | Mean ± SD | 369.9 ± 88.23 | 370.0 ± 72.44 | 379.2 ± 122.04 | 270.1 ± 71.56 |
|  | Median | 350.0 | 354.0 | 427.0 | 288.0 |
|  | Min, Max | 235.0, 585.0 | 238.0, 497.0 | 13.0, 526.0 | 162.0, 388.0 |
| Week 4 (Visit 5) | N (%) Reported | 21 (100.0%) | 21 (100.0%) | 19 (100.0%) | 16 (100.0%) |
|  | Mean ± SD | 371.6 ± 83.36 | 387.3 ± 107.39 | 430.7 ± 163.39 | 246.9 ± 95.26 |
|  | Median | 353.0 | 372.0 | 479.0 | 265.5 |
|  | Min, Max | 246.0, 535.0 | 241.0, 626.0 | 8.0, 643.0 | 40.0, 397.0 |
| Week 6 (Visit 6) | N (%) Reported | 21 (100.0%) | 21 (100.0%) | 19 (100.0%) | 16 (100.0%) |
|  | Mean ± SD | 271.9 ± 69.21 | 276.2 ± 97.28 | 279.2 ± 102.84 | 247.6 ± 95.06 |
|  | Median | 265.0 | 240.0 | 293.0 | 246.5 |
|  | Min, Max | 121.0, 414.0 | 162.0, 539.0 | 16.0, 423.0 | 40.0, 397.0 |

TABLE 8

Secondary Efficacy Analysis: Total Testosterone (ng/dL) for Intent-to-Treat Subjects

|  |  |  | Fispemifene | | | |
|---|---|---|---|---|---|---|
| Category | Study Week | Statistics | 100 mg (N = 21) | 200 mg (N = 21) | 300 mg (N = 19) | Placebo (N = 16) |
| Descriptive Summaries | Actual Value at Baseline (Visit 2) | N (%) Reported | 21 (100.0%) | 21 (100.0%) | 19 (100.0%) | 16 (100.0%) |
|  |  | Mean ± SD | 248.6 ± 68.90 | 249.1 ± 60.90 | 234.2 ± 77.69 | 218.6 ± 79.13 |
|  |  | Median | 266.0 | 253.0 | 246.0 | 227.5 |
|  |  | Min, Max | 101.0, 347.0 | 133.0, 334.0 | 17.0, 348.0 | 58.0, 334.0 |
|  | % Change from Baseline to Week 2 | N (%) Reported | 19 (90.5%) | 21 (100.0%) | 19 (100.0%) | 14 (87.5%) |
|  |  | Mean ± SD | 0.55 ± 0.366 | 0.54 ± 0.337 | 0.60 ± 0.286 | 0.24 ± 0.354 |
|  |  | Median | 0.45 | 0.48 | 0.65 | 0.09 |
|  |  | Min, Max | 0.14, 1.33 | 0.17, 1.42 | −0.24, 1.01 | −0.13, 1.03 |

TABLE 8-continued

Secondary Efficacy Analysis: Total Testosterone (ng/dL) for Intent-to-Treat Subjects

|  |  |  | Fispemifene | | | Placebo |
|---|---|---|---|---|---|---|
| Category | Study Week | Statistics | 100 mg (N = 21) | 200 mg (N = 21) | 300 mg (N = 19) | (N = 16) |
|  | % Change from Baseline to Week 4 | N (%) Reported | 21 (100.0%) | 21 (100.0%) | 19 (100.0%) | 16 (100.0%) |
|  |  | Mean ± SD | 0.60 ± 0.524 | 0.60 ± 0.390 | 0.78 ± 0.536 | 0.14 ± 0.307 |
|  |  | Median | 0.35 | 0.60 | 0.80 | 0.14 |
|  |  | Min, Max | 0.07, 1.98 | −0.14, 1.27 | −0.53, 1.81 | −0.31, 0.74 |
|  | % Change from Baseline to Week 6 | N (%) Reported | 21 (100.0%) | 21 (100.0%) | 19 (100.0%) | 16 (100.0%) |
|  |  | Mean ± SD | 0.15 ± 0.341 | 0.13 ± 0.341 | 020 ± 0.310 | 0.16 ± 0.374 |
|  |  | Median | 0.11 | 0.11 | 0.14 | 0.10 |
|  |  | Min, Max | −0.27, 1.19 | −0.38, 0.79 | −0.24, 0.77 | −0.31, 1.10 |
| P-values[1] for Comparing Treatments Over Time |  | All Arms | 0.017 | — | — | — |
|  |  | 100 mg vs. Placebo | 0.020 | — | — | — |
|  |  | 200 mg vs. Placebo | 0.023 | — | — | — |
|  |  | 300 mg vs. Placebo | 0.002 | — | — | — |

% Change from Baseline is defined as (Week 2, 4 or 6 minus Baseline) divided by Baseline. Missing values for ITT subjects are replaced via LOCF approach.
[1]P-values for comparing treatment groups over time from a repeated-measures analysis of variance model via PROC MIXED with % change as response variable and terms of treatment, visit (study week), and treatment by visit interactions.

TABLE 9

Secondary Efficacy Analysis: Sex Hormone Binding Globulin (nmol/L) for Intent to Treat Subjects

|  |  |  | Fispemifene | | | Placebo |
|---|---|---|---|---|---|---|
| Category | Study Week | Statistics | 100 mg (N = 21) | 200 mg (N = 21) | 300 mg (N = 19) | (N = 16) |
| Descriptive Summaries | Actual Value at Baseline (Visit 2) | N (%) Reported | 21 (100.0%) | 21 (100.0%) | 19 (100.0%) | 16 (100.0%) |
|  |  | Mean ± SD | 18.4 ± 6.96 | 19.5 ± 11.12 | 20.0 ± 10.28 | 16.4 ± 6.10 |
|  |  | Median | 17.0 | 18.0 | 19.0 | 15.5 |
|  |  | Min, Max | 8.5, 35.0 | 3.7, 51.0 | 5.6, 48.0 | 9.0, 30.0 |
|  | % Change from Baseline to Week 2 | N (%) Reported | 19 (90.5%) | 21 (100.0%) | 19 (100.0%) | 14 (87.5%) |
|  |  | Mean ± SD | 0.32 ± 0.211 | 0.46 ± 0.255 | 0.55 ± 0.253 | 0.017 ± 0.1299 |
|  |  | Median | 0.32 | 0.38 | 0.48 | 0.045 |
|  |  | Min, Max | 0.00, 0.85 | 0.09, 1.27 | 0.25, 1.11 | −0.286, 0.222 |
|  | % Change from Baseline to Week 4 | N (%) Reported | 21 (100.0%) | 21 (100.0%) | 19 (100.0%) | 16 (100.0%) |
|  |  | Mean ± SD | 0.35 ± 0.292 | 0.45 ± 0.338 | 0.47 ± 0.262 | −0.013 ± 0.1403 |
|  |  | Median | 0.29 | 0.41 | 0.46 | −0.028 |
|  |  | Min, Max | −0.11, 1.00 | 0.00, 1.27 | 0.05, 0.93 | −0263, 0.280 |
|  | % Change from Baseline to Week 6 | N (%) Reported | 21 (100.0%) | 21 (100.0%) | 19 (100.0%) | 16 (100.0%) |
|  |  | Mean ± SD | 0.055 ± 0.1469 | 0.065 ± 0.1886 | 0.037 ± 0.1447 | 0.010 ± 0.1164 |
|  |  | Median | 0.067 | 0.067 | 0.038 | 0.021 |
|  |  | Min, Max | −0.308, 0.294 | −0.154, 0.546 | −0.232, 0.296 | −0.263, 0.188 |
| P-values[1] for Comparing Treatments Over Time |  | All Arms | <0.001 | — | — | — |
|  |  | 100 mg vs. Placebo | <0.001 | — | — | — |
|  |  | 200 mg vs. Placebo | <0.001 | — | — | — |
|  |  | 300 mg vs. Placebo | <0.001 | — | — | — |

% Change from Baseline is defined as (Week 2, 4 or 6 minus Baseline) divided by Baseline. Missing values for ITT subjects are replaced via LOCF approach.
[1]P-values for comparing treatment groups over time from a repeated-measures analysis of variance model via PROC MIXED with % change as response variable and terms of treatment, visit (study week), and treatment by visit interactions.

TABLE 10

Secondary Efficacy Analysis: Dihydrotestosterone (pg/mL) for Intent to Treat Subjects

|  |  |  | Fispemifene | | | Placebo |
|---|---|---|---|---|---|---|
| Category | Study Week | Statistics | 100 mg (N-21) | 200 mg (N-21) | 300 mg (N-19) | (N-16) |
| Descriptive Summaries | Actual Value at Baseline (Visit 2) | N (%) Reported | 21 (100.0%) | 19 (90.5%) | 19 (100.0%) | 16 (100.0%) |
|  |  | Mean ± SD | 177.5 ± 88.58 | 185.2 ± 95.37 | 171.6 ± 76.42 | 156.5 ± 72.13 |
|  |  | Median | 180.0 | 168.0 | 179.0 | 149.0 |
|  |  | Min, Max | 50.0, 385.0 | 67.0, 398.0 | 50.0, 294.0 | 50.0, 313.0 |
|  | % Change from Baseline to Week 2 | N (%) Reported | 19 (90.5%) | 19 (90.5%) | 19 (100.0%) | 14 (87.5%) |
|  |  | Mean ± SD | 0.46 ± 0.342 | 0.50 ± 0.342 | 0.59 ± 0.387 | 0.028 ± 0.2336 |

TABLE 10-continued

Secondary Efficacy Analysis: Dihydrotestosterone (pg/mL) for Intent to Treat Subjects

| | | | Fispemifene | | | |
|---|---|---|---|---|---|---|
| | | | 100 mg | 200 mg | 300 mg | Placebo |
| Category | Study Week | Statistics | (N-21) | (N-21) | (N-19) | (N-16) |
| | | Median | 0.42 | 0.50 | 0.65 | 0.024 |
| | | Min, Max | 0.00, 1.09 | −0.08, 1.28 | 0.00, 1.62 | −0.355, 0.509 |
| | % Change from Baseline | N (%) Reported | 21 (100.0%) | 19 (90.5%) | 19 (100.0%) | 16 (100.0%) |
| | to Week 4 | Mean ± SD | 0.41 ± 0.351 | 0.68 ± 0.507 | 0.79 ± 0.504 | −0.001 ± 0.2336 |
| | | Median | 0.33 | 0.61 | 0.73 | −0.082 |
| | | Min, Max | −0.09, 0.98 | −0.04, 1.62 | 0.00, 1.63 | −0.305, 0.450 |
| | % Change from Baseline | N (%) Reported | 21 (100.0%) | 19 (90.5%) | 19 (100.0%) | 16 (100.0%) |
| | to Week 6 | Mean ± SD | 0.14 ± 0.306 | 0.16 ± 0.335 | 0.24 ± 0.366 | 0.064 ± 0.2698 |
| | | Median | 0.19 | 0.11 | 0.19 | 0.016 |
| | | Min, Max | −0.43, 0.64 | −0.54, 0.78 | −0.29, 0.98 | −0.236, 0.650 |
| P-values[1] for | | All Arms | <0.001 | — | — | — |
| Comparing | | 100 mg vs. Placebo | 0.003 | — | — | — |
| Treatments | | 200 mg vs. Placebo | <0.001 | — | — | — |
| Over Time | | 300 mg vs. Placebo | <0.001 | — | — | — |

% Change from Baseline is defined as (Week 2, 4 or 6 minus Baseline) divided by Baseline. Missing values for ITT subjects are replaced via LOCF approach.
[1]P-values for comparing treatment groups over time from a repeated-measures analysis of variance model via PROC MIXED with % change as response variable and terms of treatment, visit (study meek), and treatment by visit interactions.

TABLE 11

Secondary Efficacy Analysis: Estradiol (pg/mL) for Intent to Treat Subjects

| | | | Fispemifene | | | |
|---|---|---|---|---|---|---|
| | | | 100 mg | 200 mg | 300 mg | Placebo |
| Category | Study Week | Statistics | (N = 21) | (N = 21) | (N = 19) | (N = 16) |
| Descriptive | Actual Value at Baseline | N (%) Reported | 21 (100.0%) | 21 (100.0%) | 19 (100.0%) | 16 (100.0%) |
| Summaries | (Visit 2) | Mean ± SD | 18.2 ± 6.54 | 19.2 ± 6.23 | 20.8 ± 7.15 | 19.7 ± 6.20 |
| | | Median | 18.0 | 17.0 | 22.0 | 19.0 |
| | | Min, Max | 10.0, 34.0 | 11.0, 33.0 | 10.0, 42.0 | 10.0, 33.0 |
| | % Change from Baseline | N (%) Reported | 19 (90.5%) | 21 (100.0%) | 19 (100.0%) | 14 (87.5%) |
| | to Week 2 | Mean ± SD | 0.40 ± 0.453 | 0.36 ± 0.523 | 0.36 ± 0.343 | 0.091 ± 0.3 155 |
| | | Median | 0.32 | 0.23 | 0.33 | 0.000 |
| | | Min, Max | −0.15, 1.31 | −0.27, 1.71 | −0.45, 1.08 | −0.389, 0.765 |
| | % Change from Baseline | N (%) Reported | 21 (100.0%) | 21 (100.0%) | 19 (100.0%) | 16 (100.0%) |
| | to Week 4 | Mean ± SD | 0.37 ± 0.323 | 0.48 ± 0.556 | 0.38 ± 0.366 | 0.082 ± 0.2924 |
| | | Median | 0.31 | 0.43 | 0.29 | 0.000 |
| | | Min, Max | −0.18, 1.10 | −0.29, 1.50 | −0.23, 1.00 | −0.261, 0.750 |
| | % Change from Baseline | N (%) Reported | 21 (100.%) | 21 (100.0%) | 19 (100.0%) | 16 (100.0%) |
| | to Week 6 | Mean ± SD | 0.16 ± 0.271 | 0.21 ± 0.488 | 0.10 ± 0.305 | 0.071 ± 0.3290 |
| | | Median | 0.13 | 0.23 | 0.00 | 0.000 |
| | | Min, Max | −0.17, 0.80 | −0.33, 1.76 | −0.32, 0.77 | −0.444, 1.000 |
| P-values[1] for | | All Arms | 0.093 | — | — | — |
| Comparing | | 100 mg vs. Placebo | 0.044 | — | — | — |
| Treatments | | 200 mg vs. Placebo | 0.017 | — | — | — |
| Over Time | | 300 mg vs. Placebo | 0.083 | — | — | — |

% Change from Baseline is defined as (Week 2, 4 or 6 minus Baseline) divided by Baseline. Missing values for ITT subjects are replaced via LOCF approach.
[1]P-values for comparing treatment groups over time from a repeated-measures analysis of variance model via PROC MIXED with % change as response variable and terms of treatment, visit (study week), and treatment by visit interactions.

TABLE 12

Secondary Efficacy Analysis: LH (IU/L) for Intent to Treat Subjects

| | | | Fispemifene | | | |
|---|---|---|---|---|---|---|
| | | | 100 mg | 200 mg | 300 mg | Placebo |
| Category | Study Week | Statistics | (N = 21) | (N = 21) | (N = 19) | (N = 16) |
| Descriptive | Actual Value at Baseline | N (%) Reported | 21 (100.0%) | 21 (100.0%) | 19 (100.0%) | 16 (100.0%) |
| Summaries | (Visit 2) | Mean ± SD | 4.43 + 2.438 | 4.25 ± 2.028 | 3.62 ± 1.506 | 4.49 ± 1.699 |
| | | Median | 4.10 | 3.60 | 3.20 | 4.15 |
| | | Min, Max | 1.50, 13.50 | 1.00, 11.60 | 1.90, 8.00 | 150, 7.20 |

TABLE 12-continued

Secondary Efficacy Analysis: LH (IU/L) for Intent to Treat Subjects

| Category | Study Week | Statistics | Fispemifene | | | Placebo (N = 16) |
|---|---|---|---|---|---|---|
| | | | 100 mg (N = 21) | 200 mg (N = 21) | 300 mg (N = 19) | |
| | % Change from Baseline to Week 2 | N (%) Reported | 19 (90.5%) | 21 (100.0%) | 19 (100.0%) | 14 (87.5%) |
| | | Mean ± SD | 039 ± 0.496 | 0.52 ± 0.364 | 0.57 ± 0.414 | 0.18 ± 0.356 |
| | | Median | 0.29 | 0.54 | 0.63 | 0.03 |
| | | Min, Max | −0.40, 1.41 | −0.02, 1.23 | −0.11, 1.34 | −0.32, 0.80 |
| | % Change from Baseline to Week 4 | N (%) Reported | 21 (100.0%) | 21 (100.0%) | 19 (100.0%) | 16 (100.0%) |
| | | Mean ± SD | 0.46 ± 0.600 | 0.55 ± 0.412 | 0.57 ± 0.577 | 0.17 ± 0.295 |
| | | Median | 0.49 | 0.52 | 0.42 | 0.07 |
| | | Min, Max | −0.32, 2.03 | −0.22, 1.37 | −0.19, 1.78 | −0.21, 0.84 |
| | % Change from Baseline to Week 6 | N (%) Reported | 21 (100.0%) | 21 (100.0%) | 19 (100.0%) | 16 (100.0%) |
| | | Mean ± SD | 0.090 ± 0.3664 | 0.22 ± 0.397 | 0.16 ± 0.365 | 0.13 ± 0.362 |
| | | Median | 0.000 | 0.19 | 0.19 | 0.03 |
| | | Min, Max | −0.537, 1.000 | −0.56, 0.80 | −0.41, 0.84 | −0.32, 1.28 |
| P-values[1] for Comparing Treatments Over Time | | All Arms | 0.089 | — | — | — |
| | | 100 mg vs. Placebo | 0.200 | — | — | — |
| | | 200 mg vs. Placebo | 0.027 | — | — | — |
| | | 300 mg vs. Placebo | 0.026 | — | — | — |

% Change from Baseline is defined as (Week 2, 4 or 6 minus Baseline) divided by Baseline. Missing values for ITT subjects are replaced via LOCF approach.
[1]P-values for comparing treatment groups over time from a repeated-measures analysis of variance model via PROC MIXED with % change as response variable and terms of treatment, visit (study week), and treatment by visit interactions.

TABLE 13

Secondary Efficacy Analysis: FSH (IU/L) for Intent to Treat Subjects

| Category | Study Week | Statistics | Fispemifene | | | Placebo (N = 16) |
|---|---|---|---|---|---|---|
| | | | 100 mg (N = 21) | 200 mg (N = 21) | 300 mg (N = 19) | |
| Descriptive Summaries | Actual Value at Baseline (Visit 2) | N (%) Reported | 21 (100.0%) | 21 (100.0%) | 19 (100.0%) | 16 (100.0%) |
| | | Mean ± SD | 649 ± 3.738 | 5.91 ± 3.054 | 5.08 ± 2.931 | 7.01 ± 3.399 |
| | | Median | 5.00 | 5.20 | 4.10 | 6.35 |
| | | Min, Max | 220, 14.90 | 2.40, 14.20 | 1.80, 12.30 | 2.60, 13.10 |
| | % Change from Baseline to Week 2 | N (%) Reported | 19 (90.5%) | 21 (100.0%) | 19 (100.0%) | 14 (87.5%) |
| | | Mean ± SD | 0.29 ± 0.222 | 0.33 ± 0.147 | 0.36 ± 0.233 | 0.13 ± 0.171 |
| | | Median | 0.27 | 0.28 | 0.31 | 0.10 |
| | | Min, Max | −0.13, 0.76 | 0.03, 0.60 | −0.21, 0.78 | −0.10, 0.47 |
| | % Change from Baseline to Week 4 | N (%) Reported | 21 (100.0%) | 21 (100.0%) | 19 (100.0%) | 16 (100.0%) |
| | | Mean ± SD | 0.28 ± 0.296 | 0.32 ± 0.157 | 0.29 ± 0.206 | 0.14 ± 0.181 |
| | | Median | 0.24 | 0.33 | 0.28 | 0.13 |
| | | Min, Max | −0.09, 1.12 | 0.02, 0.58 | −0.24, 0.60 | −0.20, 0.53 |
| | % Change from Baseline to Week 6 | N (%) Reported | 21 (100.0%) | 21 (100.0%) | 19 (100.0%) | 16 (100.0%) |
| | | Mean ± SD | 0.043 ± 0.2302 | 0.050 ± 0.1657 | −0.010 ± 0.1786 | 0.084 ± 0.1797 |
| | | Median | 0.000 | 0.022 | −0.043 | 0.056 |
| | | Min, Max | −0.345, 0.610 | −0.167, 0.442 | −0.255, 0.395 | −0.205, 0.489 |
| P-values[1] for Comparing Treatments Over Time | | All Arms | 0.198 | — | — | — |
| | | 100 mg vs. Placebo | 0.141 | — | — | — |
| | | 200 mg vs. Placebo | 0.042 | — | — | — |
| | | 300 mg vs. Placebo | 0.089 | — | — | — |

% Change from Baseline is defined as (Week 2, 4 or 6 minus Baseline) divided by Baseline. Missing values for ITT subjects are replaced via LOCF approach.
[1]P-values for comparing treatment groups over time from a repeated-measures analysis of variance model via PROC MIXED with % change as response variable and terms of treatment, visit (study week), and treatment by visit interactions.

TABLE 14

Secondary Efficacy Analysis: Inhibin B (pg/mL) for Intent to Treat Subjects

| Category | Study Week | Statistics | Fispemifene | | | Placebo (N = 16) |
|---|---|---|---|---|---|---|
| | | | 100 mg (N = 21) | 200 mg (N = 21) | 300 mg (N = 19) | |
| Descriptive Summaries | Actual Value at Baseline (Visit 2) | N (%) Reported | 21 (100.0%) | 21 (100.0%) | 19 (100.0%) | 16 (100.0%) |
| | | Mean ± SD | 95.1 ± 46.32 | 105.6 ± 59.43 | 127.3 ± 75.76 | 95.4 ± 60.22 |

TABLE 14-continued

Secondary Efficacy Analysis: Inhibin B (pg/mL) for Intent to Treat Subjects

|  |  |  | Fispemifene | | | Placebo (N = 16) |
|---|---|---|---|---|---|---|
| Category | Study Week | Statistics | 100 mg (N = 21) | 200 mg (N = 21) | 300 mg (N = 19) |  |
|  |  | Median | 89.0 | 95.0 | 128.0 | 88.5 |
|  |  | Min, Max | 22.0, 191.0 | 16.0, 220.0 | 16.0, 334.0 | 16.0, 250.0 |
|  | % Change from Baseline to Week 2 | N (%) Reported | 19 (90.5%) | 21 (100.0%) | 18 (94.7%) | 14 (87.5%) |
|  |  | Mean ± SD | 0.24 ± 0.493 | 039 ± 0.534 | 0.12 ± 0.400 | 0.13 ± 0.363 |
|  |  | Median | 0.17 | 0.21 | 0.05 | 0.02 |
|  |  | Min, Max | −0.44, 1.64 | −0.22, 1.48 | −0.42, 0.97 | −0.34, 0.92 |
|  | % Change from Baseline to Week 4 | N (%) Reported | 21 (100.0%) | 21 (100.0%) | 19 (100.0%) | 15 (93.8%) |
|  |  | Mean ± SD | 0.30 ± 0.631 | 0.42 ± 0.862 | 0.016 ± 0.2904 | 0.12 ± 0.351 |
|  |  | Median | 0.09 | 0.12 | −0.012 | 0.09 |
|  |  | Min, Max | −0.61, 1.86 | −0.44, 3.40 | −0.459, 0.878 | −0.29, 1.07 |
|  | % Change from Baseline to Week 6 | N (%) Reported | 21 (100.0%) | 21 (100.0%) | 19 (100.0%) | 15 (93.8%) |
|  |  | Mean ± SD | 0.41 ± 0.572 | 0.40 ± 0.628 | 0.004 ± 0.3349 | 0.18 ± 0.583 |
|  |  | Median | 0.29 | 0.22 | −0.057 | 0.00 |
|  |  | Min, Max | −0.41, 1.40 | −0.34, 2.00 | −0.493, 0.645 | −0.63, 1.28 |
| P-values[1] for Comparing Treatments Over Time |  | All Arms | 0.097 | — | — | — |
|  |  | 100 mg vs. Placebo | 0.308 | — | — | — |
|  |  | 200 mg vs. Placebo | 0.106 | — | — | — |
|  |  | 300 mg vs. Placebo | 0.586 | — | — | — |

% Change from Baseline is defined as (Week 2, 4 or 6 minus Baseline) divided by Baseline. Missing values for ITT subjects are replaced via LOCF approach.
[1]P-values for comparing treatment groups over time from a repeated-measures analysis of variance model via PROC MIXED with % change as response variable and terms of treatment, visit (study week), and treatment by visit interactions.

TABLE 15

Secondary Efficacy Analysis: Testosterone/E2 Ratio for Intent to Treat Subjects

|  |  |  | Fispemifene | | | Placebo (N = 16) |
|---|---|---|---|---|---|---|
| Category | Study Week | Statistics | 100 mg (N = 21) | 200 mg (N = 21) | 300 mg (N = 19) |  |
| Descriptive Summaries | Actual Value at Baseline (Visit 2) | N (%) Reported | 21 (100.0%) | 21 (100.0%) | 18 (94.7%) | 16 (100.0%) |
|  |  | Mean ± SD | 15.2 ± 6.39 | 14.2 ± 5.73 | 11.5 ± 4.87 | 11.7 ± 4.68 |
|  |  | Median | 14.7 | 14.9 | 10.6 | 11.9 |
|  |  | Min, Max | 5.2, 27.0 | 6.3, 30.2 | 1.7, 23.1 | 4.6, 19.4 |
|  | % Change from Baseline to Week 2 | N (%) Reported | 19 (90.5%) | 21 (100.0%) | 18 (94.7%) | 14 (87.5%) |
|  |  | Mean ± SD | 0.21 ± 0.457 | 0.25 ± 0.418 | 0.21 ± 0.372 | 0.23 ± 0.643 |
|  |  | Median | 0.18 | 0.19 | 0.15 | 0.14 |
|  |  | Min, Max | −0.39, 1.21 | −0.29, 0.93 | −0.24, 1.43 | −0.27, 2.33 |
|  | % Change from Baseline to Week 4 | N (%) Reported | 21 (100.0%) | 21 (100.0%) | 18 (94.7%) | 16 (100.0%) |
|  |  | Mean ± SD | 0.22 ± 0.482 | 0.18 ± 0.387 | 0.33 ± 0.428 | 0.11 ± 0.403 |
|  |  | Median | 0.13 | 0.17 | 0.36 | −0.01 |
|  |  | Min, Max | −0.29, 1.57 | −0.34, 1.08 | −0.53, 1.12 | −0.31, 1.09 |
|  | % Change from Baseline to Week 6 | N (%) Reported | 21 (100.0%) | 21 (100.0%) | 18 (94.7%) | 16 (100.0%) |
|  |  | Mean ± SD | −0.002 ± 0.1993 | 0.019 ± 0.3760 | 0.12 ± 0.250 | 0.19 ± 0.633 |
|  |  | Median | 0.029 | −0.030 | 0.11 | −0.01 |
|  |  | Min, Max | −0.337, 0.411 | −0.517, 0.937 | −0.29, 0.65 | −0.40, 2.06 |
| P-values[1] for Comparing Treatments Over Time |  | All Arms | 0.923 | — | — | — |
|  |  | 100 mg vs. Placebo | 0.878 | — | — | — |
|  |  | 200 mg vs. Placebo | 0.922 | — | — | — |
|  |  | 300 mg vs. Placebo | 0.661 | — | — | — |

% Change from Baseline is defined as (Week 2, 4 or 6 minus Baseline) divided by Baseline. Missing values for ITT subjects are replaced via LOCF approach,
[1]P-values for comparing treatment groups over time from a repeated-measures analysis of variance model via PROC MIXED with % change as response variable and terms of treatment, visit (study week), and treatment by visit interactions.

The invention claimed is:

1. A method of treating erectile dysfunction, comprising administering a therapeutically effective amount of fispemifene to a subject in need thereof, the subject further suffering from secondary hypogonadism and metabolic syndrome.

2. The method of claim 1 wherein the subject has low serum total testosterone, in a range of less than about 400 ng/dL.

3. The method of claim 1 wherein the subject is insufficiently responsive to treatment with a PDE-5 inhibitor alone.

4. The method according to claim 1, wherein the therapeutically effective amount of fispemifene is about 10 mg to about 1000 mg.

5. The method of claim 1, further comprising administration of a therapeutically effective amount of a PDE-5 inhibitor.

6. The method of claim 5, wherein the PDE-5 inhibitor is sildenafil, vardenafil, or tadalafil.

7. The method of claim 5, wherein the PDE-5 inhibitor is tadalafil.

8. The method of claim 1, wherein the therapeutically effective amount of fispemifene is an amount sufficient to raise levels of testosterone, luteinizing hormone, and follicle-stimulating hormone.

9. The method of claim 1, wherein the therapeutically effective amount of fispemifene is about 10 mg to about 1000 mg administered orally.

10. The method of claim 7, wherein the therapeutically effective amount of tadalafil is in the range of 2.5 mg to 20 mg administered orally.

11. The method of claim 3, further comprising administration of a therapeutically effective amount of a PDE-5 inhibitor.

12. The method of claim 1, wherein the erectile dysfunction is treated without harmful effects on fertility.

* * * * *